(12) United States Patent
Rollinger et al.

(10) Patent No.: US 9,458,759 B2
(45) Date of Patent: Oct. 4, 2016

(54) METHOD AND SYSTEM FOR ENGINE COOLING SYSTEM CONTROL

(71) Applicant: Ford Global Technologies, LLC, Dearborn, MI (US)

(72) Inventors: John Eric Rollinger, Troy, MI (US); William Russell Goodwin, Farmington Hills, MI (US); Casey Dietrich, Ypsilanti, MI (US); Matt Gerow, Alpena, MI (US); Scott Steadmon Thompson, Sterling Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 126 days.

(21) Appl. No.: 14/583,437

(22) Filed: Dec. 26, 2014

(65) Prior Publication Data
US 2016/0186650 A1    Jun. 30, 2016

(51) Int. Cl.
| | | |
|---|---|---|
| *F01P 11/18* | (2006.01) | |
| *F01P 7/14* | (2006.01) | |
| *F01P 11/04* | (2006.01) | |

(52) U.S. Cl.
CPC ............... *F01P 11/18* (2013.01); *F01P 7/14* (2013.01); *F01P 11/04* (2013.01)

(58) Field of Classification Search
CPC ............ G01F 23/296; G01F 23/2961; G01F 23/2962; G01F 23/2965; G01S 15/12; F01P 11/18; F01P 7/14; F01P 11/04
See application file for complete search history.

(56) References Cited

U.S. PATENT DOCUMENTS

| | | | |
|---|---|---|---|
| 3,964,567 A | 6/1976 | McGinty | |
| 4,964,090 A | 10/1990 | McCarthy | |
| 5,765,433 A * | 6/1998 | Johnson | G01F 17/00 73/290 V |
| 6,573,732 B1 * | 6/2003 | Reimer | B60K 15/077 324/644 |
| 7,542,870 B2 * | 6/2009 | Reimer | G01F 23/2962 702/155 |
| 8,583,387 B2 | 11/2013 | Murphy | |
| 2011/0301883 A1 * | 12/2011 | Murphy | G01F 23/2962 702/55 |
| 2013/0103284 A1 | 4/2013 | Gordon | |
| 2014/0196536 A1 * | 7/2014 | Murphy | G01F 23/296 73/290 V |

FOREIGN PATENT DOCUMENTS

EP    2037110 A2    3/2009

OTHER PUBLICATIONS

Styron, Joshua P. et al., "Method and System for Engine Cooling System Control", U.S. Appl. No. 14/583,328, filed Dec. 26, 2014, 88 pages.

(Continued)

*Primary Examiner* — Hung Q Nguyen
*Assistant Examiner* — Xiao Mo
(74) *Attorney, Agent, or Firm* — Julia Voutyras; Alleman Hall McCoy Russel & Tuttle LLP

(57) ABSTRACT

Methods and systems are providing for improving engine coolant level estimation to reduce engine overheating. The level of fluid in a coolant overflow reservoir is inferred based on the fluid level in a hollow vertical standpipe fluidically coupled to the reservoir at top and bottom locations, while the fluid level in the standpipe is estimated based on output from an ultrasonic signal transmitted by a sensor positioned in a recess at the bottom of the vertical standpipe. Sensor power usage is optimized based on the ratio of first order and higher order harmonic echo times in the raw data set generated by the sensor.

19 Claims, 19 Drawing Sheets

(56) References Cited

OTHER PUBLICATIONS

Rollinger, John, E. et. al., "Method and System for Engine Cooling System Control", U.S. Appl. No. 14/583,366, filed Dec. 26, 2014, 87 pages.

Rollinger, John, E. et. al., "Method and System for Engine Cooling System Control", U.S. Appl. No. 14/583,393, filed Dec. 26, 2014, 88 pages.

Rollinger, John, E. et. al., "Method and System for Engine Cooling System Control", U.S. Appl. No. 14/583,414, filed Dec. 26, 2014, 87 pages.

* cited by examiner

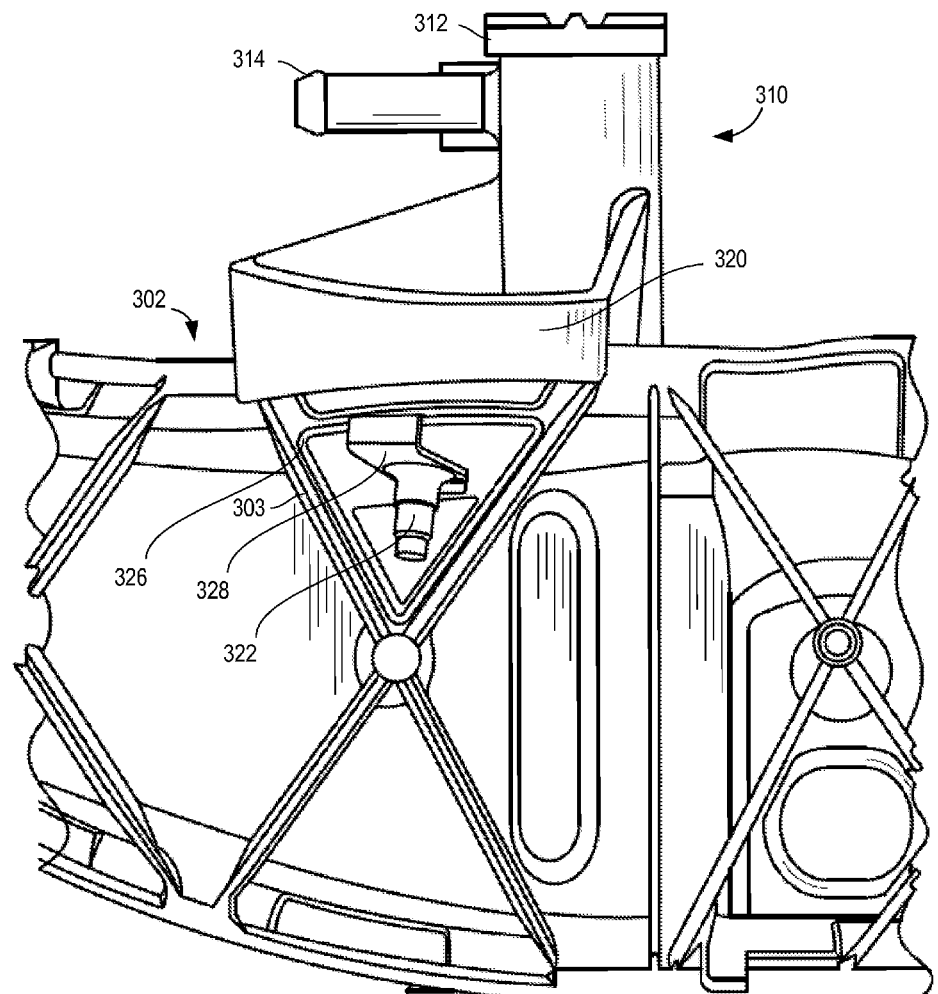
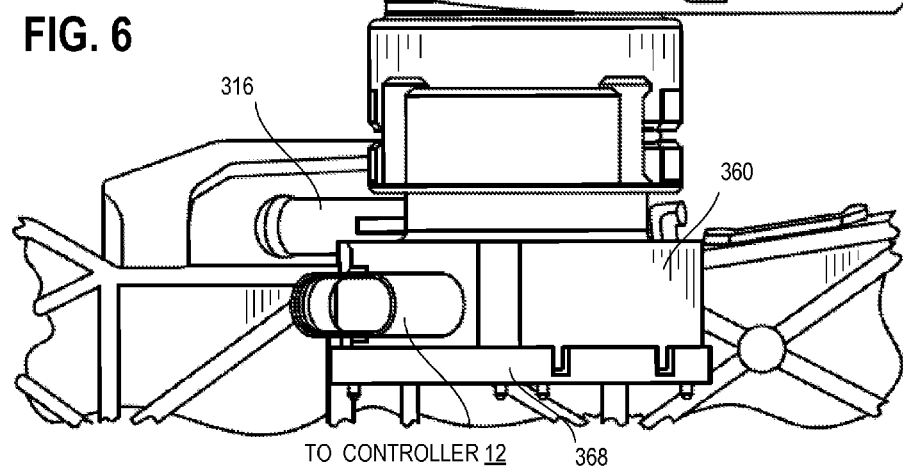
FIG. 6

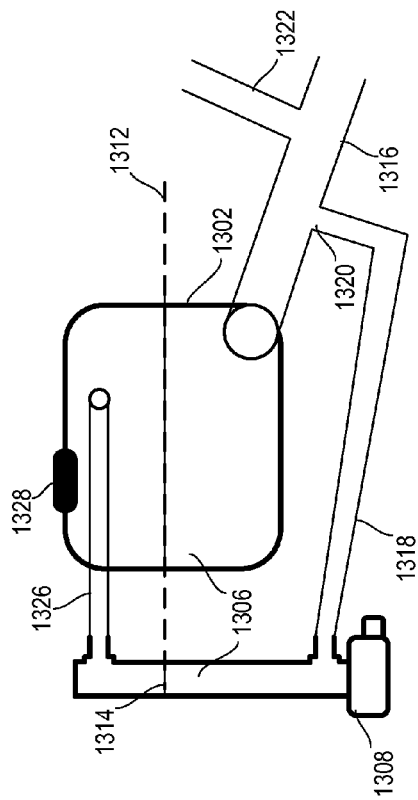
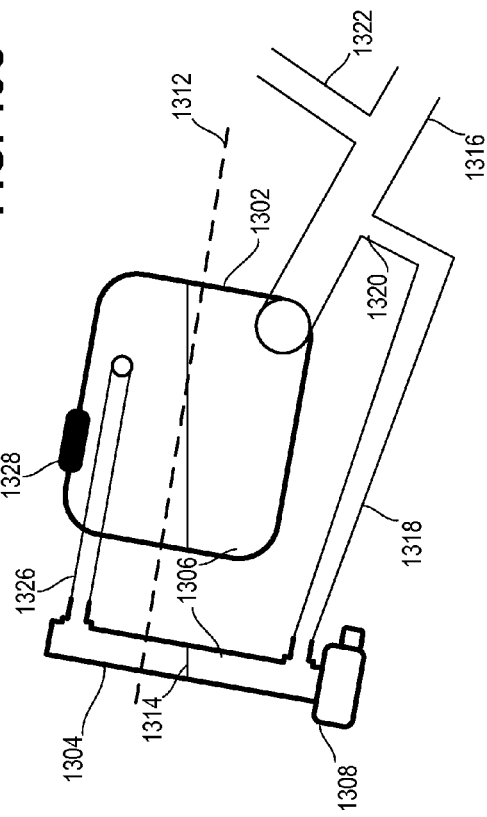
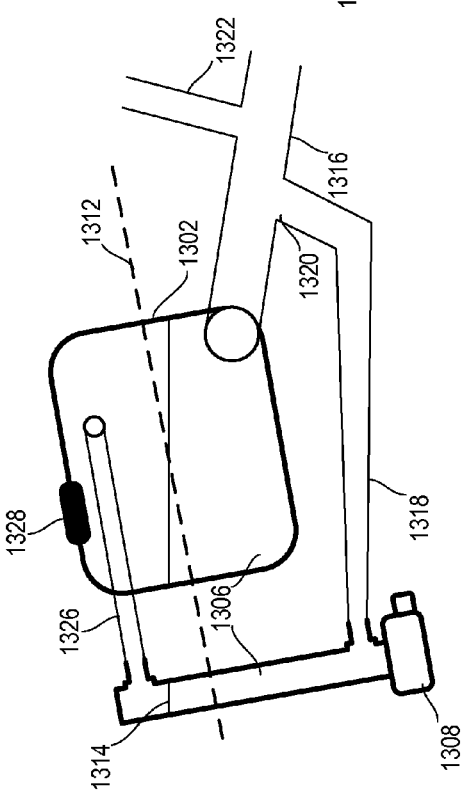

METHOD AND SYSTEM FOR ENGINE COOLING SYSTEM CONTROL

FIELD

The present application relates to methods and systems for inferring a fluid level in a coolant overflow container (or degas bottle), and adjusting engine operation, based on a fluid level estimated in a vertical hollow standpipe fluidically coupled to the overflow container.

BACKGROUND AND SUMMARY

Vehicles may include cooling systems configured to reduce overheating of an engine by transferring the heat to ambient air. Therein, coolant is circulated through the engine block to remove heat from the engine, the heated coolant then circulated through a radiator to dissipate the heat. The cooling system may include various components such as a coolant reservoir coupled to the system for degassing and storing coolant. A pressurized reservoir that also serves to separate entrained air from the coolant is typically called a degas bottle. When the temperature of coolant anywhere in the system rises, thermal expansion of the coolant causes pressure to rise in the degas bottle as the trapped air volume reduces. Pressure relief can be achieved by releasing air from the degas bottle through a valve that is typically mounted in the fill cap. Then, when the temperature and pressure of coolant drops below atmospheric pressure in the degas bottle, air may be drawn back into the bottle through another valve that is often mounted in the fill cap.

If the coolant level in bottle is too low, the air volume will be too large to build sufficient pressure to prevent boiling and cavitation at the water pump inlet. At low fluid levels, the degas bottle will also no longer be able to separate air from the coolant and air can be drawn into the cooling system, again leading to poor cooling performance. If an overflow system is employed instead of an active degas system, a similar loss in cooling system performance can be realized when fluid levels are low.

Various approaches may be used to estimate fluid level in a reservoir. One example approach described by Murphy in U.S. Pat. No. 8,583,387 uses an ultrasonic fluid level sensor installed at the bottom of a reservoir to estimate a fluid level of the reservoir. However, the inventors herein have recognized that in such a cooling system, the dimensions of the coolant reservoir may vary based on the temperature of coolant contained in the reservoir. As a result, there may be inconsistencies in the estimated coolant level. Additionally, due to the location of the sensor at the bottom of the container, at low coolant levels, it may be unclear whether the fluid level in the reservoir is low or empty. Further still, it may be difficult to differentiate actual low coolant levels from incorrect coolant level estimation due to sensor degradation. In another example approach, described by Gordon et al in US 20130103284, the sensor is coupled to a coolant reservoir hose. One issue with such an approach is that the sensor can only detect the presence of coolant at that location in the circuit. Critical components of the power train may not be receiving coolant despite the presence of coolant in one of the coolant reservoir hoses, particularly if that hose is isolated from the cooling system by a valve (e.g., the engine thermostat hose). Further, while an indication of low coolant fluid level is received, engine temperature control may already be degraded due to substantial emptying of the coolant reservoir.

In one approach, the above issue may be at least partly addressed by a method for a coolant system, comprising: periodically transmitting a sensor signal from a bottom to a top of a vertical, hollow tube fluidically coupled to the reservoir at each of the bottom and the top; receiving an echo of the transmitted signal; and adjusting a power of the periodically transmitted signals based on an average duration elapsed between the transmitting and the receiving. In this way, the amount of power supplied to the piezoelectric transducer may be selectively increased to maintain the number of first-order echo returns above a first threshold, or selectively decreased to maintain the number of higher-order echo returns below a second threshold and maintain energy efficiency.

As one example, an engine coolant system may include a vertical tube aligned with a coolant overflow reservoir, the tube housing an ultrasonic sensor. The vertical tube may be coupled to the coolant reservoir at each of a top and bottom location via hoses, coolant flowing between the tube and the reservoir via the hoses. The hoses may be connected such that a headspace is generated between the top of the fluid level in the vertical tube and the top of the tube. In addition, the hoses may be connected such that the top of the vertical tube is arranged at a lower height than the top of the coolant reservoir, thereby allowing the sensor to more reliably estimate the fluid level in the reservoir and distinguish between low and empty coolant level states. The sensor, positioned inside a recess at the bottom of the vertical tube, may transmit a signal to the top of the vertical tube, an echo of the signal being received at the sensor after being reflected off the top of the tube. The signal may be transmitted periodically and based on an average echo time (which is the time elapsed between the signal being transmitted and an echo of the signal being received), the coolant level in the vertical tube may be estimated. This estimate may then be used to infer the coolant level in the reservoir. As one example, the sensor may receive first-order echo returns for each emitted pulse, but receive a number of second and third-order echo returns above a threshold number. In response to the detection of higher order echoes, the power supplied to the piezoelectric element may be decreased at a slower rate. At a later time, if the number of first-order echo returns falls below a threshold number, the power supplied to the piezoelectric element may be increased at a faster rate. In another example, the sensor may receive no first-order echo returns in a measurement period, in which case the power may be increased to the physical maximum until a threshold number of first-order echo returns are received in a measurement period.

In this way, an accuracy and reliability of determining a coolant level of a coolant overflow reservoir can be increased. By inferring the coolant level of the reservoir based on an estimated coolant level of a standpipe coupled to the reservoir, wherein the coolant level of the stand pipe is based on an echo time of an ultrasonic signal transmitted by a sensor of the stand pipe, inaccuracies in coolant level estimation due to distortion of an in-tank sensor output during thermal fluctuations, or vehicle motion, is reduced. By adjusting the energy output of the ultrasonic sensor based on the detection of first-order and second order echo times, sensor output optimization is achieved. Specifically, first order echo values can be improved while reducing the power requirement of the sensor. Overall, power reduction benefits are achieved without degrading the accuracy and reliability of coolant level estimation.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF FIGURES

FIG. 6 shows a third alternate view of the part of the cooling system in FIG. 3, highlighting the affixing of the standpipe to the vehicle frame.

FIGS. 13A-13C show the divergence of the fluid levels in the vertical standpipe and the coolant reservoir based on vehicle attitude.

DETAILED DESCRIPTION

Figure 1:
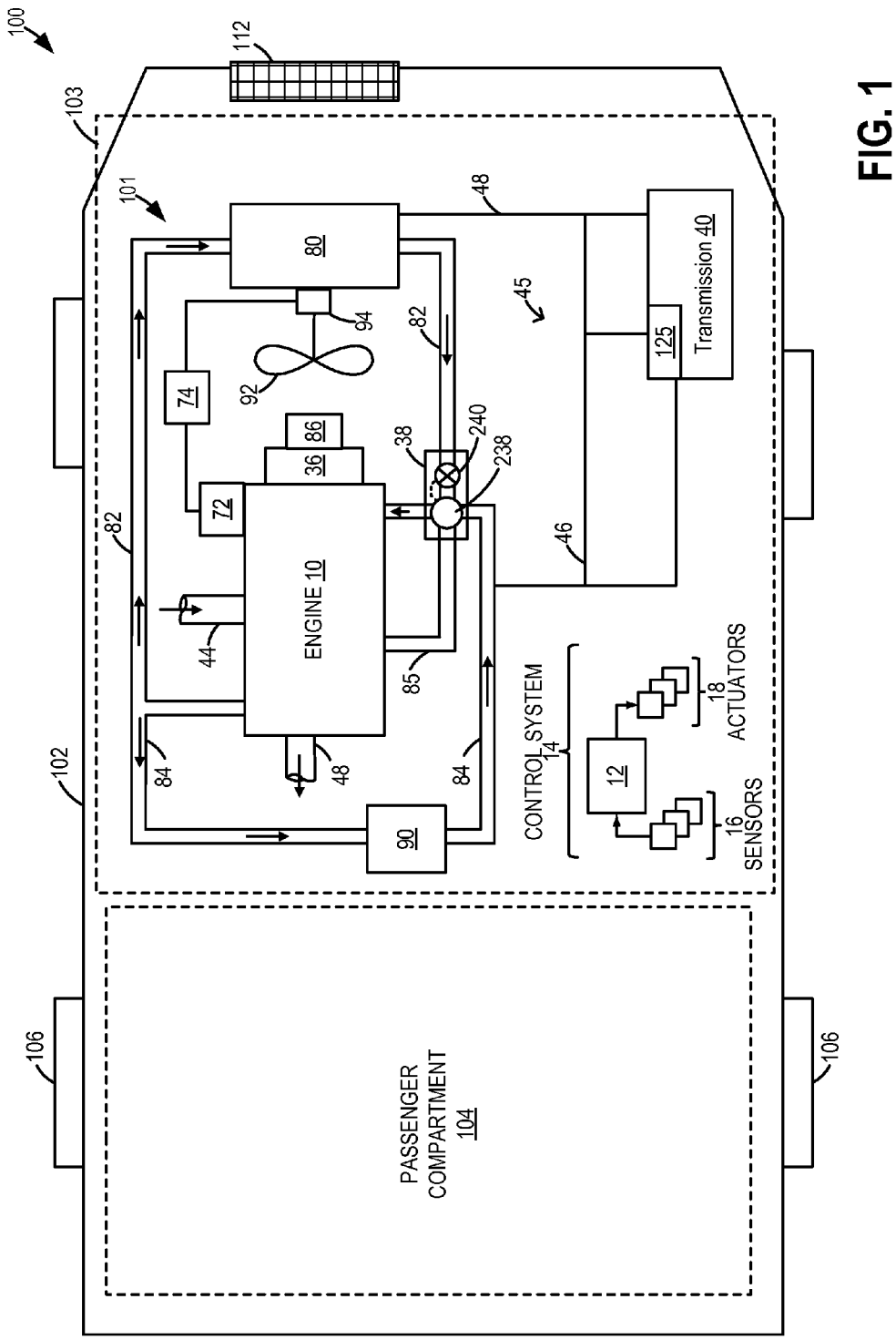
FIG. 1 shows an engine system including an engine cooling system.
Figure 2:
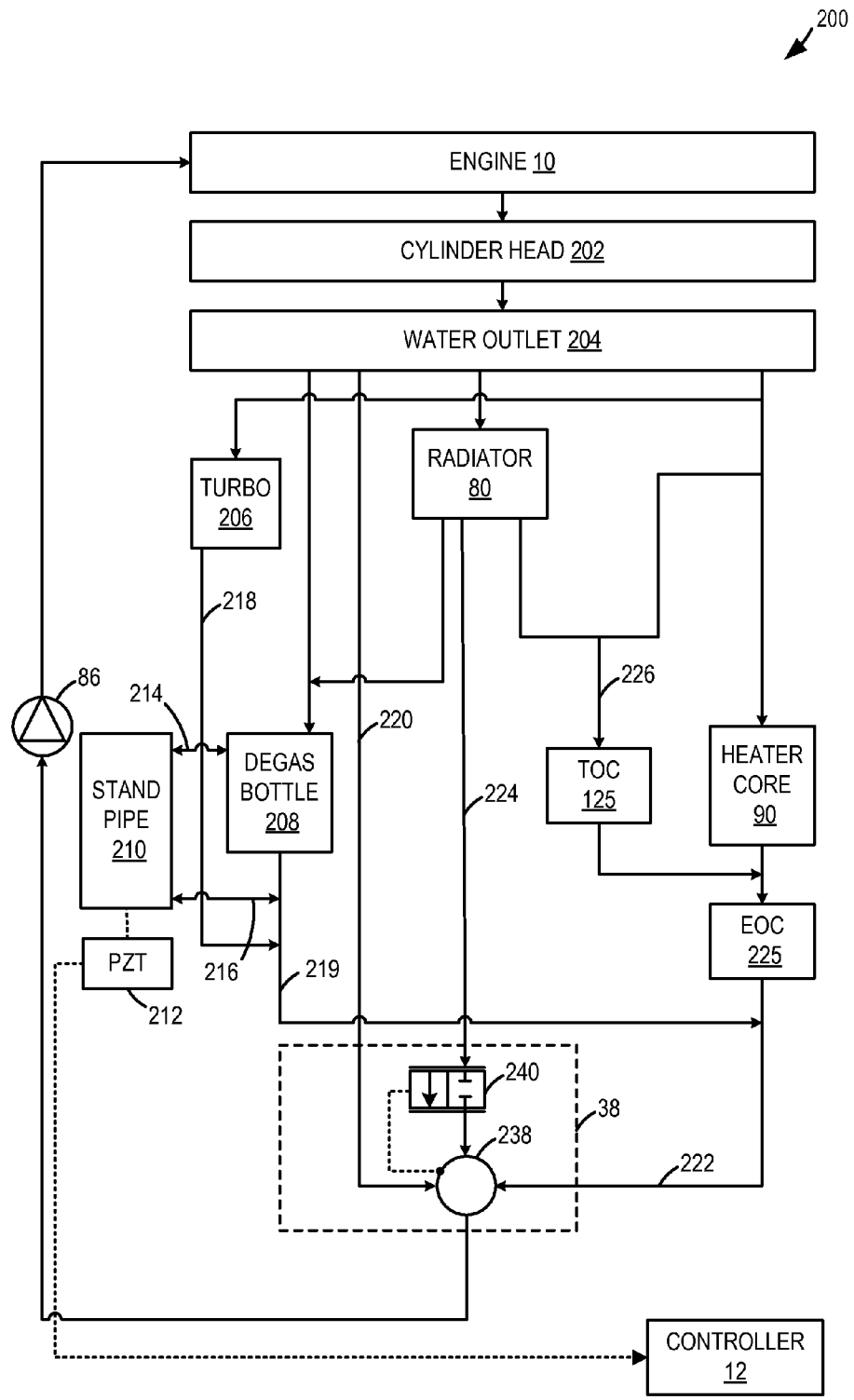
FIG. 2 shows a block diagram of an engine cooling system.

The following description relates to systems and methods for controlling an engine of a vehicle, the engine having a cooling system such as that of FIGS. 1-2. The cooling system may include a coolant overflow reservoir, herein also referred to as a degas bottle, fluidly connected to a narrow vertical standpipe, as discussed at FIGS. 3-8. The vertical standpipe may include a level sensor broadcasting information to an engine controller for determining an amount of coolant within the standpipe, as elaborated at FIGS. 9-12. The controller may also estimate an amount of coolant within the degas bottle (herein also referred to as a bulk coolant level), based on the amount of coolant within the standpipe (herein also referred to as a local coolant level) and various motion parameters, as described at FIGS. 13-17. Based on the estimate of coolant, the controller may indicate a coolant state, and based on the coolant state, restrictions may be placed on engine operating parameters, as discussed at FIGS. 18-19. In this way, bulk coolant levels may be inferred more accurately even during slosh events. In addition, low coolant levels may be more reliably detected and engine operating parameters may be restricted accordingly to prevent overheating of the engine.

FIG. 1 shows an example embodiment of a vehicle system 100 including a vehicle cooling system 101 in a motor vehicle 102. Vehicle 102 has drive wheels 106, a passenger compartment 104 (herein also referred to as a passenger cabin), and an under-hood compartment 103. Under-hood compartment 103 may house various under-hood components under the hood (not shown) of motor vehicle 102. For example, under-hood compartment 103 may house internal combustion engine 10. Internal combustion engine 10 has a combustion chamber which may receive intake air via intake passage 44 and may exhaust combustion gases via exhaust passage 48. Engine 10 as illustrated and described herein may be included in a vehicle such as a road automobile, among other types of vehicles. While the example applications of engine 10 will be described with reference to a vehicle, it should be appreciated that various types of engines and vehicle propulsion systems may be used, including passenger cars, trucks, etc.

Under-hood compartment 103 may further include cooling system 101 that circulates coolant through internal combustion engine 10 to absorb waste heat, and distributes the heated coolant to radiator 80 and/or heater core 90 via coolant lines (or loops) 82 and 84, respectively. In one example, as depicted, cooling system 101 may be coupled to engine 10 and may circulate engine coolant from engine 10 to radiator 80 via engine-driven water pump 86, and back to engine 10 via coolant line 82. Engine-driven water pump 86 may be coupled to the engine via front end accessory drive (FEAD) 36, and rotated proportionally to engine speed via a belt, chain, etc. Specifically, engine-driven pump 86 may circulate coolant through passages in the engine block, head, etc., to absorb engine heat, which is then transferred via the radiator 80 to ambient air. In one example, where pump 86 is a centrifugal pump, the pressure (and resulting flow) produced by the pump may be increased with increasing crankshaft speed, which in the example of FIG. 1, may be directly linked to the engine speed. In some examples, engine-driven pump 86 may operate to circulate the coolant through both coolant lines 82 and 84.

The temperature of the coolant may be regulated by a thermostat 38. Thermostat 38 may include a temperature sensing element 238, located at the junction of cooling lines 82, 85, and 84. Further, thermostat 38 may include a thermostat valve 240 located in cooling line 82. As elaborated in further detail at FIG. 2, the thermostat valve remain closed until the coolant reaches a threshold temperature, thereby limiting coolant flow through the radiator until the threshold temperature is reached.

Coolant may flow through coolant line 84 to heater core 90 where the heat may be transferred to passenger compartment 104. Then, coolant flows back to engine 10 through valve 122. Specifically, heater core 90, which is configured as a water-to-air heat exchanger, may exchange heat with the circulating coolant and transfer the heat to the vehicle passenger compartment 104 based on operator heating demands. As such, heater core may also be coupled to a vehicle HVAC system (or heating, ventilation, and air conditioning system) that includes other components such as a heater fan, and an air conditioner (not shown).

Based on a cabin heating/cooling request received from the operator, the HVAC system may warm cabin air using the heated coolant at the heater core to raise cabin temperatures and provide cabin heating. One or more blowers (not shown) and cooling fans may be included in cooling system 101 to provide airflow assistance and augment a cooling airflow through the under-hood components. For example, cooling fan 92, coupled to radiator 80, may be operated to provide cooling airflow assistance through radiator 80. Cooling fan 92 may draw a cooling airflow into under-hood compartment 103 through an opening in the front-end of vehicle 102, for example, through grill shutter system 112. Such a cooling air flow may then be utilized by radiator 80 and other under-hood components (e.g., fuel system components, batteries, etc.) to keep the engine and/or transmission cool. Further, the air flow may be used to reject heat from a vehicle air conditioning system. Further still, the airflow may be used to improve the performance of a turbocharged/supercharged engine that is equipped with intercoolers that reduce the temperature of the air that goes into the intake manifold/engine. In one example, grill shutter system 112 may be configured with a plurality of louvers (or fins, blades, or shutters) wherein a controller may adjust a position of the louvers to control an airflow through the grill shutter system.

Cooling fan 92 may be coupled to, and driven by, engine 10, via alternator 72 and system battery 74. Cooling fan 92 may also be mechanically coupled to engine 10 via an optional clutch (not shown). During engine operation, the engine generated torque may be transmitted to alternator 72 along a drive shaft (not shown). The generate torque may be used by alternator 72 to generate electrical power, which may be stored in an electrical energy storage device, such as system battery 74. Battery 74 may then be used to operate an electric cooling fan motor 94.

Vehicle system 100 may further include a transmission 40 for transmitting the power generated at engine 10 to vehicle wheels 106. Transmission 40, including various gears and clutches, may be configured to reduce the high rotational speed of the engine to a lower rotational speed of the wheel, while increasing torque in the process. To enable temperature regulation of the various transmission components, cooling system 101 may also be communicatively coupled to a transmission cooling system 45. The transmission cooling system 45 includes a transmission oil cooler 125 (or oil-to-water transmission heat exchanger) located internal or integral to the transmission 40, for example, in the transmission sump area at a location below and/or offset from the transmission rotating elements. Transmission oil cooler 125 may have a plurality of plate or fin members for maximum heat transfer purposes. Coolant from coolant line 84 may communicate with transmission oil cooler 125 via conduit 46. In comparison, coolant from coolant line 82 and radiator 80 may communicate with transmission oil cooler 125 via conduit 48.

FIG. 1 further shows a control system 14. Control system 14 may be communicatively coupled to various components of engine 10 to carry out the control routines and actions described herein. For example, as shown in FIG. 1, control system 14 may include an electronic digital controller 12. Controller 12 may be a microcomputer, including a microprocessor unit, input/output ports, an electronic storage medium for executable programs and calibration values, random access memory, keep alive memory, and a data bus. As depicted, controller 12 may receive input from a plurality of sensors 16, which may include user inputs and/or sensors (such as transmission gear position, gas pedal input, brake input, transmission selector position, vehicle speed, vehicle acceleration, vehicle attitude, engine speed, mass airflow through the engine, ambient temperature, intake air temperature, etc.), cooling system sensors (such as coolant temperature, coolant level, coolant level sensor circuit board temperature, cylinder head temperature, fan speed, passenger compartment temperature, ambient humidity, thermostat output, etc.), and others. Further, controller 12 may communicate with various actuators 18, which may include engine actuators (such as fuel injectors, an electronically controlled intake air throttle plate, spark plugs, etc.), cooling system actuators (such as the various valves of the cooling system), and others. In some examples, the storage medium may be programmed with computer readable data representing instructions executable by the processor for performing the methods described below as well as other variants that are anticipated but not specifically listed.

Now turning to FIG. 2, it shows an example embodiment 200 of the cooling system of FIG. 1 with the various valves, loops, and heat exchangers.

Coolant may be circulated at thermostat 38 from various loops. As such, thermostat 38 is configured with a temperature sensing element 238 for estimating a temperature of coolant circulating at the thermostat, while thermostat valve 240, communicatively coupled to the temperature sensing element, is configured to open only when the temperature is above a threshold. In one example, thermostat valve 240 may be a mechanically actuated valve, such as a wax plug for the actuation force/displacement, that opens when coolant sensed at the temperature sensing element (the wax) is above the threshold temperature.

Coolant may circulate along a first bypass loop 220 from engine 10 towards thermostat 38. From there, the coolant may be pumped back to the engine by pump 86. Coolant may also circulate along a second heater loop 222 from engine 10 via heater core 90 and engine oil cooler 225 towards thermostat 38. From there, the coolant may be pumped back to the engine by pump 86. Coolant may also circulate from engine 10, through radiator 80, via third loop 224, to thermostat 38, based on the state of the thermostat valve 240. Specifically, when thermostat valve 240 is open, coolant may circulate though radiator 80, and then through thermostat valve 240. The flow of coolant through the radiator may allow heat from the circulating hot coolant to be dissipated to the ambient air by the radiator fan. After flowing through the thermostat valve, coolant may be pumped back towards the engine by pump 86. Coolant may circulate along a fourth coolant loop 226 from one of radiator 80 and water outlet 204, through transmission oil cooler 125, and then to engine oil cooler 225.

Coolant may flow from water outlet 204 and radiator 80 toward degas bottle 208, which may serve as a coolant reservoir within cooling system 200. Degas bottle 208 may be fluidly connected to vertically-oriented standpipe 210 via upper level sensor hose 214 and lower level sensor hose 216, as further described in reference to FIGS. 3-7. Upper level sensor hose may connect the top of degas bottle 208 to the top of vertical standpipe 210, and may be configured to allow air to flow between the two. Lower level sensor hose 216 may be connected to degas bottle 208 via degas bottle outlet hose 216, and may be configured to allow coolant to flow between degas bottle 208 and vertical standpipe 210. Vertical standpipe 210 may include a piezoelectric coolant level sensor 212, electronically connected to controller 12.

When the fluid in the cooling system heats up, it expands, causing the pressure to build up. For cooling systems with overflow bottles, the radiator cap may be the only place where this pressure can escape. As such, the setting of the spring on the radiator cap determines the maximum pressure in the cooling system. When the pressure reaches 15 psi, for example, the pressure pushes a valve of the radiator cap open, allowing pressurized coolant to escape from the cooling system. This coolant flows through the overflow tube of the radiator into the overflow bottle. Thus, this arrangement keeps air out of the coolant system. When the radiator cools back down, a vacuum is created in the cooling system that pulls open a spring loaded valve, sucking coolant back in from the bottom of the overflow bottle into the radiator.

While overflow systems control pressure by allowing coolant to be exchanged across a valve, active degas systems control pressure by allowing air to be exchanged across a valve. In degas systems, coolant thermal expansion causes fluid to flow into the degas bottle, thereby increasing air pressure within the degas bottle. When the air pressure within the bottle exceeds an upper threshold pressure, for example 21 psi, the pressure opens a valve allowing air to escape. In one example, this valve may be located in the fill cap of the reservoir (e.g., degas bottle cap 304 at FIG. 3). If air has been released from the system, the next time the system cools back to ambient temperatures, the pressure in the degas bottle will be below atmospheric pressure. In this condition, another valve located in the fill cap will open to allow ambient air to re-enter the degas bottle. The degas bottle is given its name due to the fact that it separates air that is entrained in the coolant. Some coolant from various local high points in the cooling system is allowed to flow through vent tubes back to the degas bottle.

Cooling system 200 may further include a turbocharger 206. Coolant may circulate from water outlet 204, through turbocharger 206, and toward degas bottle outlet hose 219 via turbo outlet hose 218. Turbo outlet hose 218 may be connected to degas bottle outlet hose 219 downstream of the connection between lower level sensor hose 216 and degas bottle outlet hose 219. In this way, high-temperature coolant and/or vapor carried by turbo outlet hose 218 may not affect fluid transfer between degas bottle 208 and vertical standpipe 210.

One or more temperature sensors may be coupled to the cooling system, at the engine hot water outlet, to estimate a coolant temperature. For example, coolant temperature may be estimated by an engine coolant temperature (ECT) sensor positioned to be in contact with the heated coolant. Alternatively, coolant temperature may be estimated by a cylinder head temperature (CHT) sensor positioned on the engine block, for example, positioned a few millimeters of aluminum away from the flowing engine coolant in the cylinder head. Coolant temperature may also be estimated within vertical standpipe 210, and a circuit board temperature may be estimated within the circuit board of coolant level sensor 212, as further described in reference to FIG. 7.

As elaborated herein, the vertical standpipe may be fluidically coupled to the coolant overflow reservoir such that a level of coolant in the reservoir equilibrates with the level of coolant in the vertical standpipe. Consequently, a controller may be configured to infer the level of coolant in the degas bottle based on the level of coolant in the vertical standpipe. This enables accurate coolant level estimation without incurring issues associated with the use of a level sensor in the degas bottle. Further, the coolant level in the vertical standpipe may be used to adjust engine operation so as to reduce engine overheating resulting from low coolant levels in the degas bottle.

Figure 3:
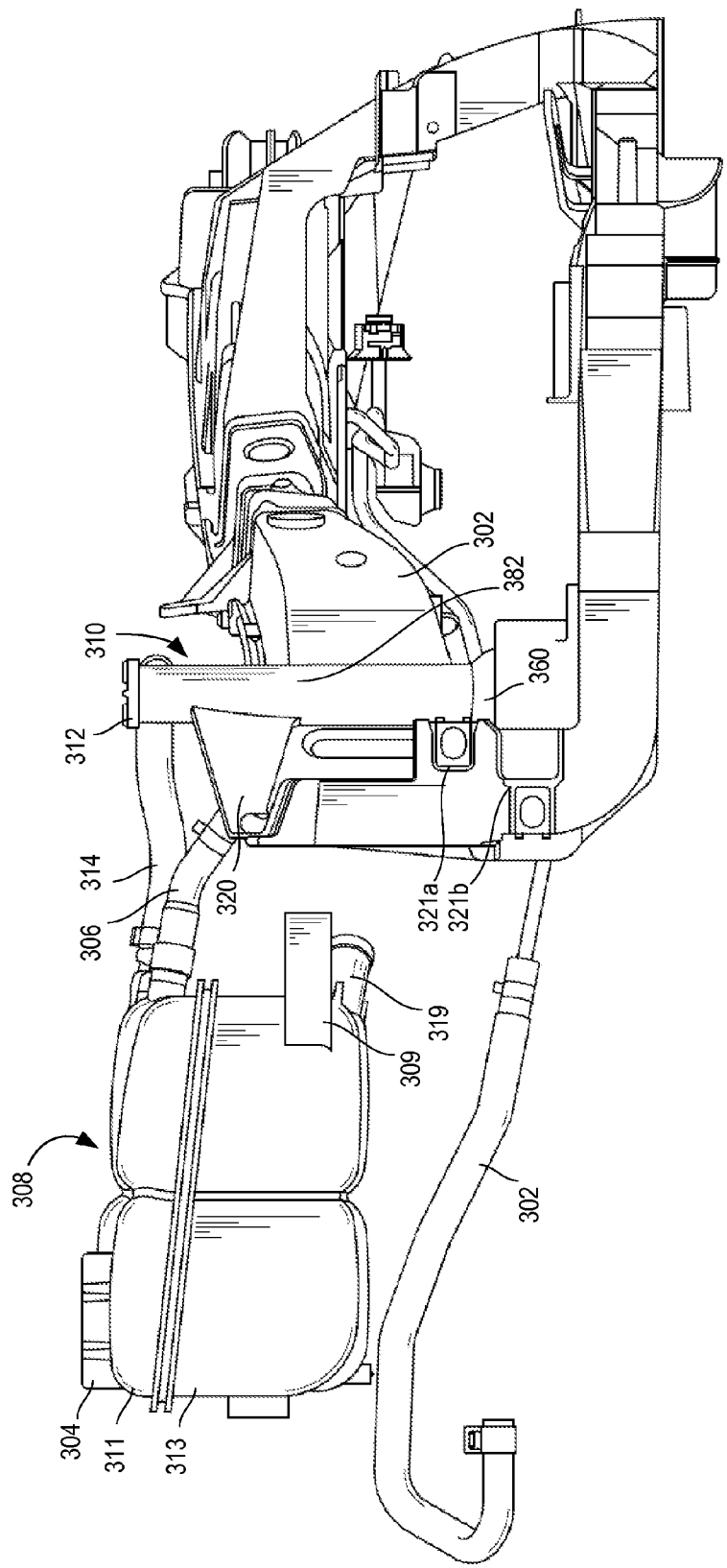
FIG. 3 shows part of an example cooling system, including a coolant reservoir fluidly coupled to a standpipe, the standpipe affixed to the vehicle frame.

FIG. 3 provides one view of the positioning of the vertical standpipe relative to the degas bottle and vehicle frame. Vertical standpipe, indicated generally at 310, is affixed to frame 302 via several components within standpipe mounting support 320, as described in further detail with reference to FIGS. 4, 5, 6 and 7. Vertical standpipe 310 may be further affixed to frame 302 via lower standpipe mounting supports 321a and 321b. The position of vertical standpipe 310 within the underhood environment is based on several criteria, including but not limited to ensuring space for routing upper level sensor hose 314 and lower level sensor hose 316 between vertical standpipe 310 and degas bottle 308 and mounting the standpipe to a strong and rigid support in order to avoid damaging vibrations. Additionally, the distance between the standpipe and the degas bottle is minimized to reduce the effect of vehicle acceleration and attitude on the difference in the standpipe fluid level and the degas bottle fluid level. In this preferred embodiment, the standpipe is be aligned with the lateral centerline of the degas bottle, thereby minimizing the influence of lateral acceleration and side-hill attitudes on the difference in fluid levels between the standpipe and degas bottle. As depicted in FIG. 3, the lateral direction is in and out of the page. Furthermore, the longitudinal distance (from left to right in FIG. 3) between the degas bottle and the vertical standpipe may be such that longitudinal acceleration and uphill/downhill attitudes provide fluctuations in the vertical standpipe fluid level, thereby providing the ability to confirm continuous sensor function.

Vertical standpipe mounting supports 320, 321 may be included as part of standpipe wall 382. Alternatively, the standpipe may be attached to standpipe wall 382 via one or more of a bolt, weld, etc. Vertical standpipe 310 is affixed such that its major axis is aligned with the gravitational force when the vehicle is at rest on a level plane. Vertical standpipe 310 and degas bottle 308 have a fixed relative positioning. The orientation of vertical standpipe 310 is configured such that the major axis of vertical standpipe is parallel to the vertical axis of degas bottle. That is to say, vertical standpipe 310 and degas bottle 308 may be configured to have a common level plane at their top surfaces. However, a bottom surface of the vertical standpipe may be arranged to be positioned lower than the bottom surface of the degas bottle. This particular configuration may ensure that a minimum threshold level coolant is present in the standpipe even when the coolant level in the degas bottle is close to empty. Such a configuration may be utilized because ultrasonic level sensors cannot measure below a minimum level. If the sensor is placed such that its minimum level is below the degas bottle outlet, any coolant in the degas bottle will be within the measurement range of the sensor. As such, the risk of the degas bottle running empty and causing engine overheating is reduced. In this way, a coolant level may be defined by a common horizontal plane cutting across both degas bottle 308 and vertical standpipe 310 when the vehicle is at rest on a level plane (as further described with reference to FIG. 4).

Vertical standpipe 310 may include a standpipe cap 312, an ultrasonic level sensor for measuring a coolant level (not pictured), and sensor housing 360. Vertical standpipe 310 is fluidly coupled to degas bottle 308 via upper level sensor hose 314 and lower level sensor hose 316. Specifically, upper level sensor hose 314 is positioned to allow air to flow between the top of vertical standpipe 310 and the top of degas bottle 308, and lower level sensor hose 316 is positioned to allow coolant to flow between the bottom of vertical standpipe 310 and the bottom of degas bottle 308. In this way, the fluid level between vertical standpipe 310 and degas bottle 308 may reach an equilibrium level when the vehicle is at rest, facilitating a comparison of a coolant level within the vertical standpipe and a coolant level in the degas bottle.

Degas bottle 308 includes degas bottle cap 304, degas inlet hose 306, and degas outlet hose 319 in addition to upper level sensor hose 314. Degas bottle 308 may comprise an upper piece 311 and a lower piece 313. In alternate embodiments, degas bottle 308 may comprise a single piece or more than two pieces. Degas bottle 308 may be affixed to any suitably high and rigid structure in such a way that degas bottle 308 is substantially level. Being substantially level includes being at an attitude wherein the top surface extends along a plane that is substantially perpendicular to the direction of gravity, for example within 5 degrees of perpendicular along each axis of extension. As one example, degas bottle 308 may be affixed to the inner fender via degas bottle mounting support 309. In one example, degas bottle mounting support 309 may be included as part of lower degas bottle piece 313. In other examples, degas bottle mounting support 309 may be attached to lower degas bottle piece 313 via a fastening mechanism. In further examples, degas bottle mounting support 309 may instead be attached to or be included as part of upper degas bottle piece 311. When affixed to degas bottle 308, degas bottle cap 304 may prevent coolant in the coolant reservoir from evaporating and escaping into the atmosphere. When degas bottle cap 304 is removed from degas bottle 308, an opening on the top of degas bottle 308 for supplying more coolant to the system may be exposed. Coolant may also be introduced into degas bottle 308 from other cooling system components via degas bottle inlet hose 306. For example, the inlet hose may direct coolant into the degas bottle from the radiator. In some examples, degas bottle cap 304 may include a valve, such as a pressure relief valve or a spring activated valve. When the fluid in the radiator heats up, such as due to extensive engine heating, the coolant expands, causing the pressure in the cooling system to increase. The cooling system pressure may escape via degas bottle fill cap 304. Specifically, the maximum pressure in the degas bottle may be determined via a spring-loaded valve in degas bottle fill cap 304. When the pressure reaches a threshold, such as 21 psi, the pressure pushes open the valve in degas bottle fill cap 304, allowing pressurized air to escape from the degas bottle to the underhood environment. When the system cools back down, a vacuum is created that draws air back in from the underhood environment via another valve in degas bottle fill cap 304.

Figure 4:
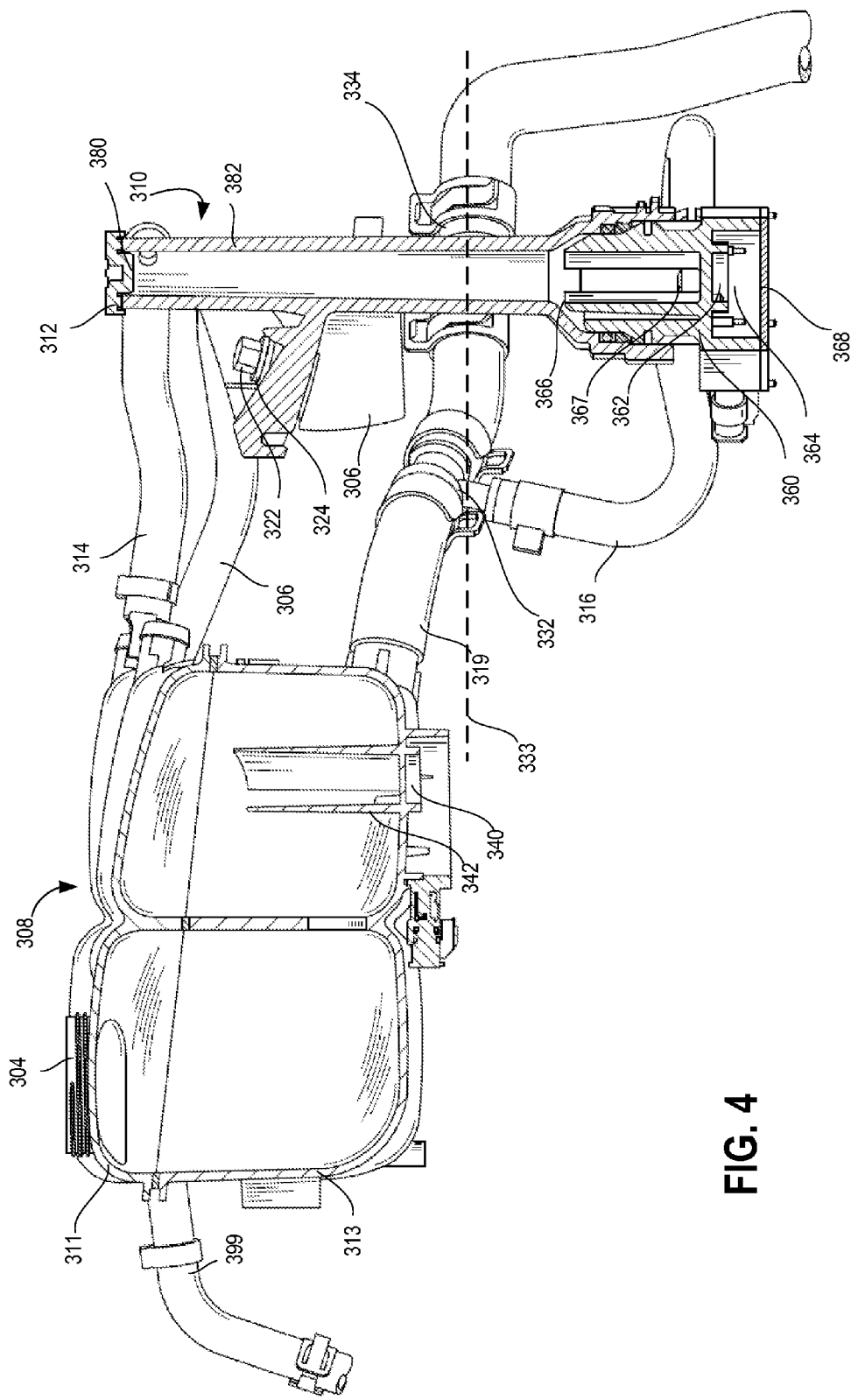
FIG. 4 shows an alternate view of the part of the cooling system in FIG. 3, highlighting features of the fluid coupling and of the affixing of the standpipe.

FIG. 4 provides an alternative view of part of a cooling system, and further details the fluidic coupling of degas bottle 308 and vertical standpipe 310. A sensor 340 may be affixed to the bottom of degas bottle 308 to measure fluid levels in the degas bottle directly. Sensor 340 may be positioned within sensor housing 342. Sensor 340 may be connected to the electronic control system, and enabled to communicate with controller 12 via the controller area network (not shown).

Lower level sensor hose 316 is coupled to degas bottle outlet hose 319 via T-joint 332. T-joint 332 is oriented so that the 90-degree branching from outlet hose 319 is downward such that any entrained bubbles in hose 319 tend to bypass hose 316. Further, when coolant is absent from degas bottle 308 and degas bottle outlet hose 319, a volume of coolant may remain "trapped" in lower level sensor hose 314 and vertical standpipe 310. This trapped volume of coolant may be measurable by ultrasonic level sensor 362. Additionally, a connection may be made between a turbo outlet hose (218 at FIG. 2) and degas bottle outlet hose 319 downstream of T-joint 332 (obscured at FIG. 4 by vertical standpipe 310). This connection may be made by a second T-joint 334 oriented so that the 90-degree branching from degas bottle outlet hose 319 is upward, anti-parallel to the branching of T-joint 332. In this way, hot and/or vaporized coolant generated by return flow from turbo outlet hose 218 (the return flow varying as a function of engine speed), may not affect the difference in coolant level between degas bottle 308 and vertical standpipe 310. Lower level sensor hose 316 may be further coupled to the side of vertical standpipe 310, at a level below a blanking distance associated with ultrasonic level sensor 362 (as further discussed below in reference to FIGS. 7 and 11).

Vertical standpipe 310 is positioned such that the bottom of standpipe 310 is below the bottom of degas bottle 308 and below T-joint 332. As a result, if the coolant level in degas bottle 308 approaches the bottom of the bottle or falls below the bottom of the bottle, the corresponding local coolant level in standpipe 310 may remain at a specified level substantially above ultrasonic level sensor (ULS) 362. The specified level may be based on the level of a horizontal plane extending from the top of T-joint 332. In this way, if the local coolant level in the standpipe is estimated to be zero, a degradation of the coolant system such as a disconnected hose may be indicated, and if the local coolant level in the standpipe is estimated to be within a threshold distance of the specified level, an empty degas bottle may be indicated.

As shown in FIG. 4, vertical standpipe 310 is affixed to frame 302 in such a way that the top of the vertical standpipe occupies the same horizontal plane as the top of degas bottle 308. Vertical standpipe 310 has a larger vertical extent than degas bottle 308, and consequently the bottom of vertical standpipe 310 is below the bottom of degas bottle 308. As such, when degas bottle 308 is empty, a level of coolant may remain in vertical standpipe 310, providing a medium interface off of which ultrasonic pulses from ULS 362 may reflect. At fluid equilibrium, the local coolant level in vertical standpipe 310 that corresponds to an empty degas bottle may be defined by a horizontal plane extending the top of T-joint 332, as depicted by coolant level line 333 at FIG. 4. In this way, a specified level measurement in vertical standpipe 310 may be associated with an empty bulk coolant level in degas bottle 308, allowing for an empty bulk coolant level measurement to be differentiated from a condition such as a disconnected hose, which may induce an empty local coolant level in vertical standpipe 310.

Vertical standpipe 310 may be equipped with standpipe cap 312. Standpipe cap 312 may be configured to fit in the top of vertical standpipe 310 such that the major axis of standpipe cap 312 is parallel to the major axis of vertical standpipe 312. Standpipe cap 312 may have a smooth surface 380, which may aid in the reflection of sound waves such as those emitted by ultrasonic level sensor 362. In one example, standpipe cap 312 may be manufactured via a spin welding technique. Vertical standpipe 310 may be a cylindrical shell with a sufficiently small horizontal cross section in order to serve as a waveguide for ultrasonic sound waves. As a non-limiting example, the horizontal cross section of vertical standpipe 310 may be approximately 17.25 millimeters in diameter, and slightly larger than the sensing element of the ultrasonic level sensor. Vertical standpipe wall 382 may be composed of a smooth, rigid plastic, for example a PA66 material with 30% glass fill.

Ultrasonic level sensor (ULS) 362 may be a piezoelectric transducer element capable of both sending and receiving ultrasonic pulse signals. ULS 362 may be affixed to the bottom of vertical standpipe 310 firmly within sensor housing 360, and configured to emit sound pulses upward through the cavity of the pipe. ULS 362 may be electronically connected to ULS circuit board 364. ULS circuit board 364 may physically extend beyond the extent of ULS 362 and be in electronic communication with an engine controller (e.g., 12 of FIGS. 1-2). In a non-limiting example, sensor 340 may also be an ultrasonic level sensor configured to make direct estimates of coolant level in degas bottle 308. Sensor housing 360 may be sealed to upper standpipe wall 382 with an o-ring and retained with a metal spring clip 336 to allow quick assembly of the two halves of the standpipe wall. Sensor housing 360 may be made of a material with a coefficient of thermal expansion closer to that of ULS 362 when compared to that of upper standpipe 382, for example PPS GF30. Lower standpipe cover 368 may be attached to the bottom of sensor housing 360, protecting any sensor components from the environment. The cavity surrounding circuit board 364 and ULS 362 may be filled with flexible potting compound to further enhance environmental isolation.

Figure 5:
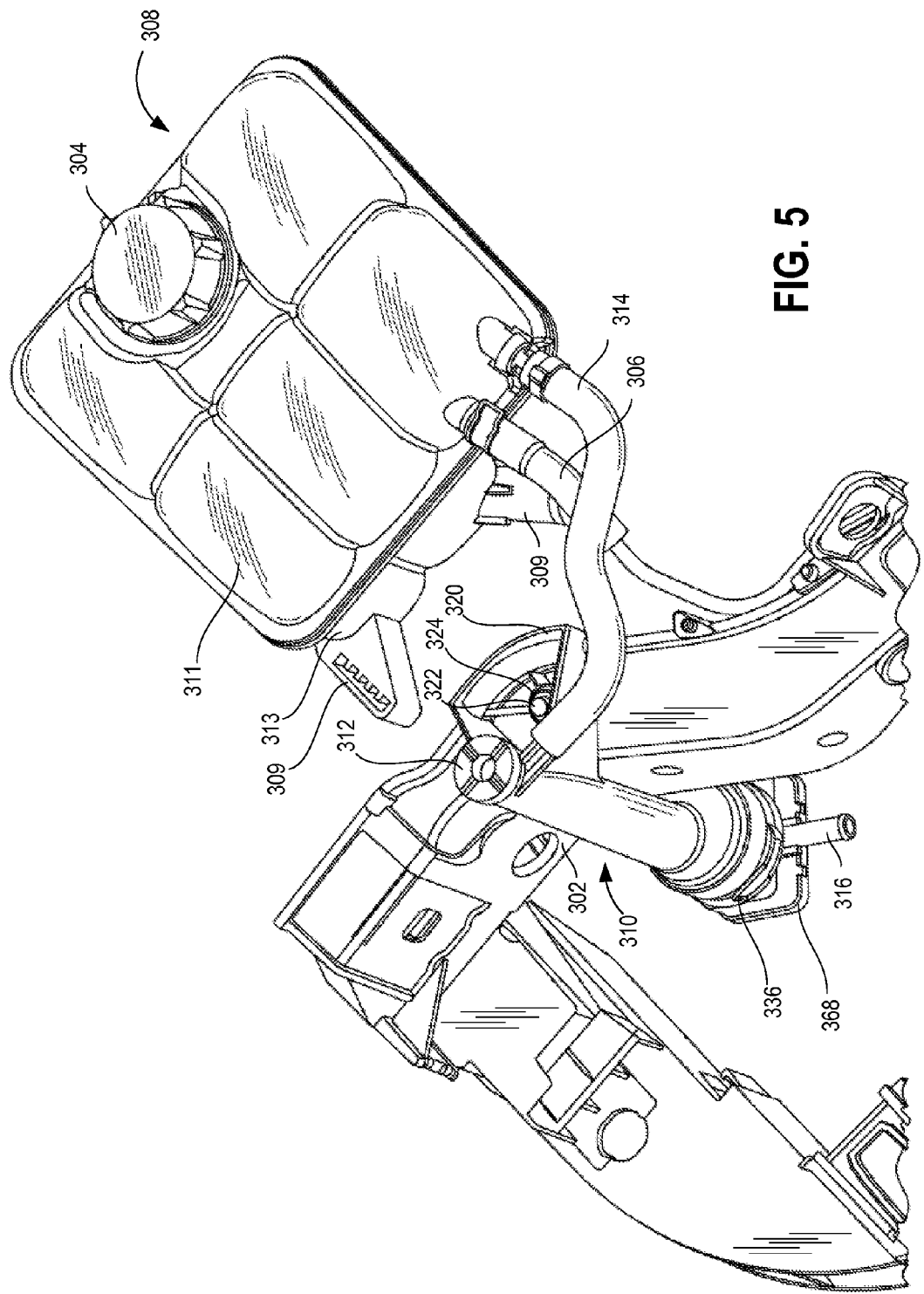
FIG. 5 shows a second alternate view of the part of the cooling system in FIG. 3.

Continuing at FIG. 5, a bird's-eye view depicting the relative positioning of degas bottle 308, vertical standpipe 310, and frame 302 is provided. Degas bottle mounting support, shown here as attached to lower degas bottle piece 313, may include a hole with several teeth to allow sufficient compliance for assembly while maintaining an interference fit after assembly. Upper level sensor hose 314 is shown extending horizontally between upper degas bottle piece 311 and the top of vertical standpipe 310.

As shown, vertical standpipe 310 may include an upper mounting support 320 extending horizontally over frame 302 and one or more lower mounting supports (not shown) extending horizontally below frame 302, while vertical standpipe is affixed alongside a vertical face of frame 302. Standpipe mounting fastener 322 is shown extending vertically from within upper mounting support 320 and through frame 302, restricting movement of vertical standpipe 310. Standpipe mounting fastener 322 may extend through metal load limiter 324 above frame 302, thereby avoiding a joint clamp load reduction which may occur over time due to creep in upper mounting support 320.

Spring retaining clip 336, located on the upper part of vertical standpipe 310, may be configured to provide robust retention and allow quick assembly of the two halves of vertical standpipe 310. Lower standpipe cover 368 is shown affixed to the bottom of vertical standpipe 310, and may shield ULS 362 and ULS circuit board 364 from the environment. As depicted herein, lower level sensor hose 316 is coupled to vertical standpipe 310 below spring retaining clip 336 and above lower standpipe cover 368.

Turning now to FIG. 6, the mounting of vertical standpipe 310 to frame 302 is depicted in greater detail. Frame 302 includes several cross-shaped support structures 303 between an upper face and a lower face of the frame. Within a cavity of one of the cross-shaped support structures 303, a mounting wedge 326 may be inserted to aid with mounting vertical standpipe 310 to frame 302. Mounting wedge 326 may be constructed to fit within an inner lattice of the cross-shaped support structure. For example, where the inner lattice has a substantially triangular shape, the mounting wedge may also be configured to have a matching triangular shape such that a snug fit is achieved. The top of mounting wedge 326 may be in direct contact with the bottom of an upper face of frame 302. Standpipe mounting fastener 322 may extend vertically from above frame 302, through metal load limiter 324, through standpipe mounting support 320, through a cavity in frame 302, and through a cavity in mounting wedge 326. Standpipe mounting fastener 322 may be coupled to mounting wedge 368 via J-clip 328. In this way, by coupling standpipe mounting support 320 to mounting wedge 326 housed within a cross-shaped support structure 303, stability of the position of vertical standpipe 310 in relation to frame 302 may be improved.

As shown, vertical standpipe 310 may extend substantially below the section of frame 302 to which it is affixed. Sensor housing 360 may extend horizontally, beneath frame 302, from vertical standpipe 310. Sensor housing 360 may be include a cavity to accept lower level sensor hose 316, and may include an electrical connection to controller 12.

Figure 7:
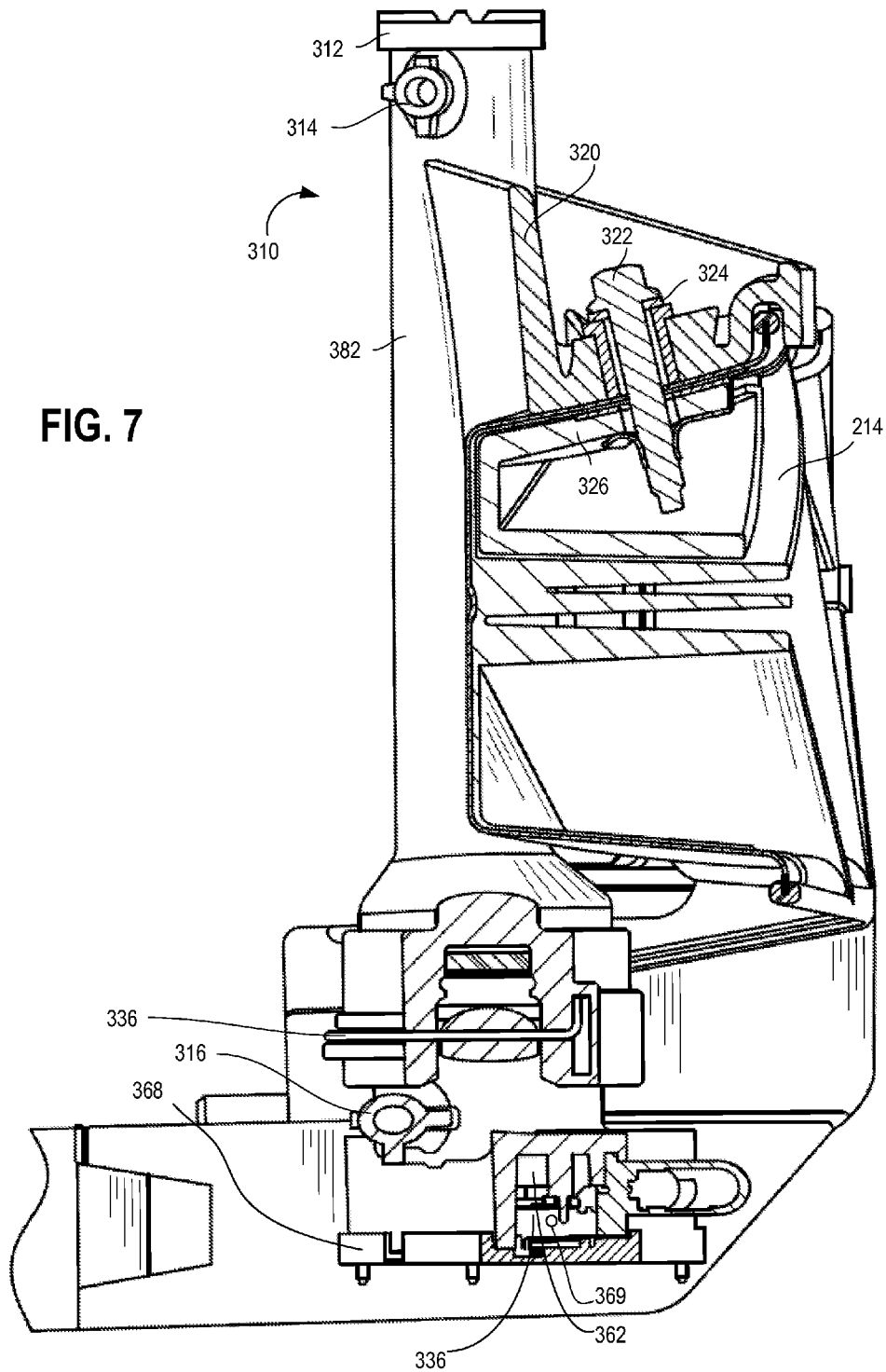
FIG. 7 shows a fourth alternate view of the part of the cooling system in FIG. 3, highlighting an ultrasonic level sensor within the standpipe and the affixing of the standpipe to the vehicle frame.

FIG. 7 provides a cross-sectional view of vertical standpipe 310, the configuration of ULS 362 and sensor housing 360, and the configuration of the upper mounting structure including mounting support 320 and mounting fastener 322. Vertical standpipe 310 is configured to couple to upper level sensor hose 314 along standpipe wall 382 adjacent to standpipe cap 312. Vertical standpipe 310 is further configured to couple to lower level sensor hose 316 just above ULS circuit board 364.

Mounting support 320 may be included as part of vertical standpipe wall 382, as shown. Mounting fastener 322 may be oriented perpendicularly to the bottom face of mounting support 320 and the top face of mounting wedge 326. Mounting fastener 322 may be a suitable fastening mechanism such as a bolt or screw.

Turning to the lower section of vertical standpipe 310, ULS circuit board 364 is shown electrically connected to ULS 362, coolant temperature sensor 367 (shown in FIG. 4), and circuit board temperature sensor 369. Coolant temperature sensor 367 may be positioned above ULS circuit board 364, and ULS circuit board temperature sensor 369 may be positioned below ULS circuit board 364. Temperature sensors 367 and 369 may be configured to periodically or continuously estimate temperatures of coolant within vertical standpipe 310 and of ULS circuit board 364, respectively. In one example, ULS circuit board temperature sensor 369 may be a surface-mounted thermistor affixed to the surface of ULS circuit board 364.

Ultrasonic level sensor 362 is configured to periodically produce sound waves for developing usable sensor data. In some embodiments ULS 362 may be configured to produce a set of multiple ultrasonic pulses (e.g., five pulses), spaced far enough apart that the pulses have enough time to travel the length of the standpipe and return to the sensor (based on length and speed of sound in fluid) before another pulse is sent out (e.g., 5-8 milliseconds between pulses), and produce a set periodically every total time of pulses seconds (e.g., every 100 milliseconds). ULS 362 may produce these sound signals continuously during conditions where the ignition state is in an engine running mode. ULS 362 is a send/ receive device, and accordingly is configured to receive sound waves. When ULS 362 is placed in vertical standpipe 310 and fluid is present in the standpipe, pulses produced by ULS 362 will be reflected by a fluid-air interface or by a vertical standpipe cap 312 and travel back toward ULS 362. If the energy of the returning pulse is above a lower threshold energy, the returning pulse will transmit a portion of its energy and may be received by ULS 362. The term first-order echo may herein also be used to refer to this returning pulse. Further, the term echo may herein refer to this returning pulse unless specified otherwise. In some sensors, the returning pulses will reflect on the bottom of the fluid cavity and travel to the fluid-air interface and reflect a second time. These waves will then travel back down toward ULS 362. This second harmonic return, herein also referred to as a second-order echo, may also be detected and can be used for signal verification and more complex operation.

Ultrasonic level sensor circuit board 364 may include memory with instructions to adjust a power level supplied to ULS 362 based on the energy associated with ultrasonic pulse signals received by ULS 362. For example, as described in further detail with reference to FIG. 10, when the energy associated with a set of ultrasonic pulse signals is greater than an upper threshold or when the number of second-order echoes associated with a set of pulses is greater than a threshold number, ULS circuit board 364 may be controlled (e.g., by engine controller 12 at FIG. 1) to decrease the power supplied to ULS 362 for emitting ultrasonic pulses. As another example, when the energy associated with a set of ultrasonic pulse signals is less than a lower threshold, ULS circuit board 364 may be controlled (e.g., by engine controller 12 at FIG. 1) may increase the power supplied to ULS 362 for emitting ultrasonic pulses. The pulse energy being less than a lower threshold may include no ultrasonic pulse being detected when a pulse is expected to be detected. ULS circuit board 364 is configured to measure time, and may include programs in memory configured to capture timestamps of ultrasonic pulses received by ULS 362. ULS circuit board 364 is further configured to estimate temperatures of the assembly and fluid via temperature sensors 367 and 369, respectively (e.g., via thermistor voltage measurements from sensors 367 and 369). In this way, ULS circuit board 364 may produce improved estimates of a standpipe coolant level based on ultrasonic pulse times and temperature estimates. ULS circuit board 364 may be configured to transmit data to controller 12 via a CAN bus, including but not limited to temperature estimates from sensors 367 and 369, ultrasonic pulse timestamps, ultrasonic pulse energy levels, and sensor-processed standpipe coolant level estimates (as further described with reference to FIG. 11).

ULS 362 may be further configured to broadcast information to an engine controller (such as controller 12 of FIG. 1) via a controller area network, as indicated. In one example, ULS 362 may be a one-way or broadcast-only device on the CAN.

Figure 8:
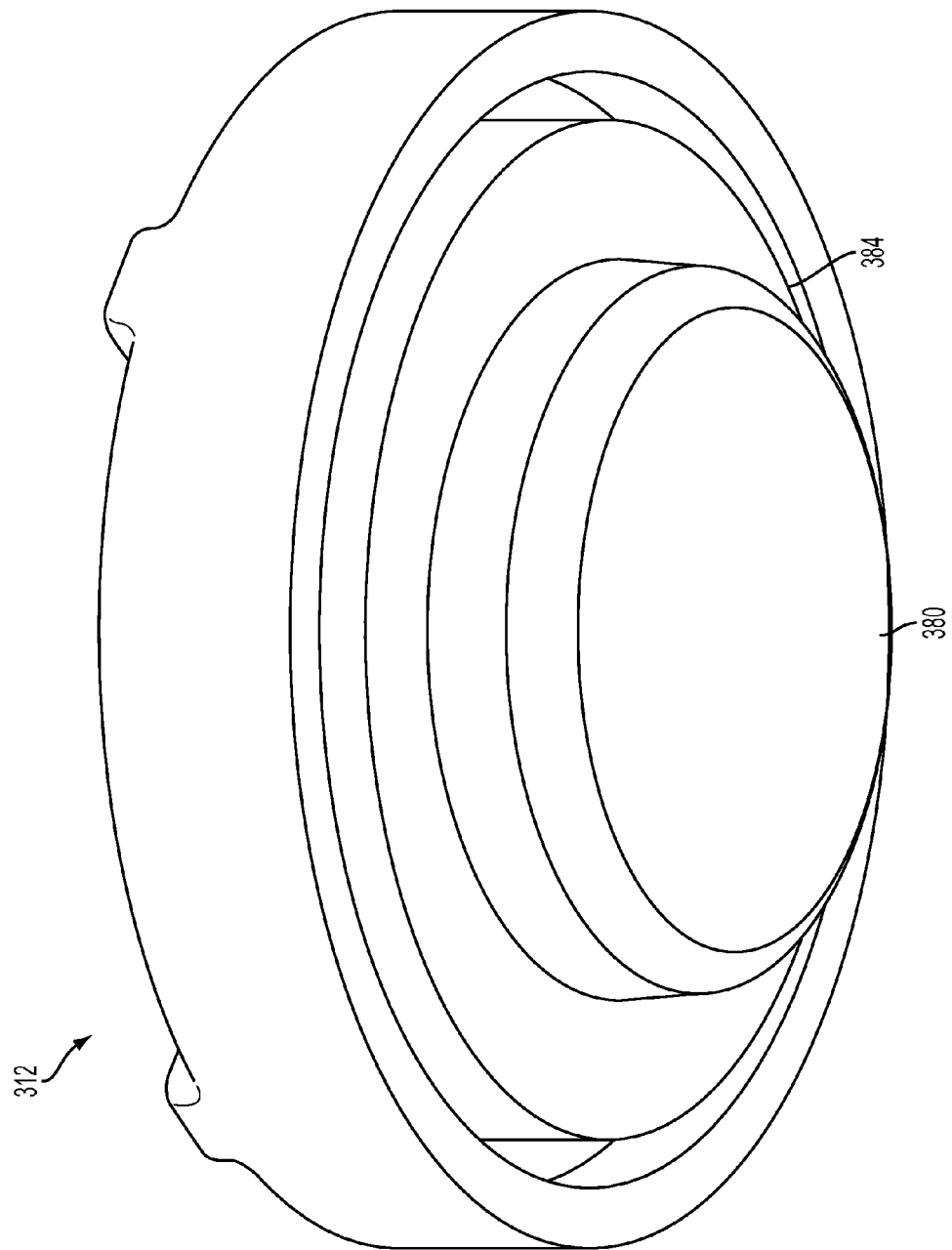
FIG. 8 shows a cap configured to fit on the top of a vertical standpipe.

FIG. 8 depicts a detailed view of standpipe cap 312. Standpipe cap 312 may be manufactured via spin-welding. Standpipe cap 312 may be cylindrical and include a circumferential groove 384 configured to accept and rest on the top of vertical standpipe wall 382. Standpipe cap surface 380 may be within the area encompassed by circumferential groove 384. Standpipe cap surface 380 may be constructed to be smooth, flat, and parallel to the emitting surface of ULS 362. In this way, standpipe cap surface 380 may efficiently reflect sound waves emitted from the ULS at the bottom of the standpipe. By improving the efficiency of sound reflection, the accuracy of fluid level estimation in the vertical standpipe is increased when the standpipe is full of fluid. If cap surface 380 were rough or angled with respect to ULS 362, reflected sound may be scattered away from ULS 362 such that the standpipe would appear empty. As such, this improves the reliability of coolant level estimation in the degas bottle.

Figure 9:
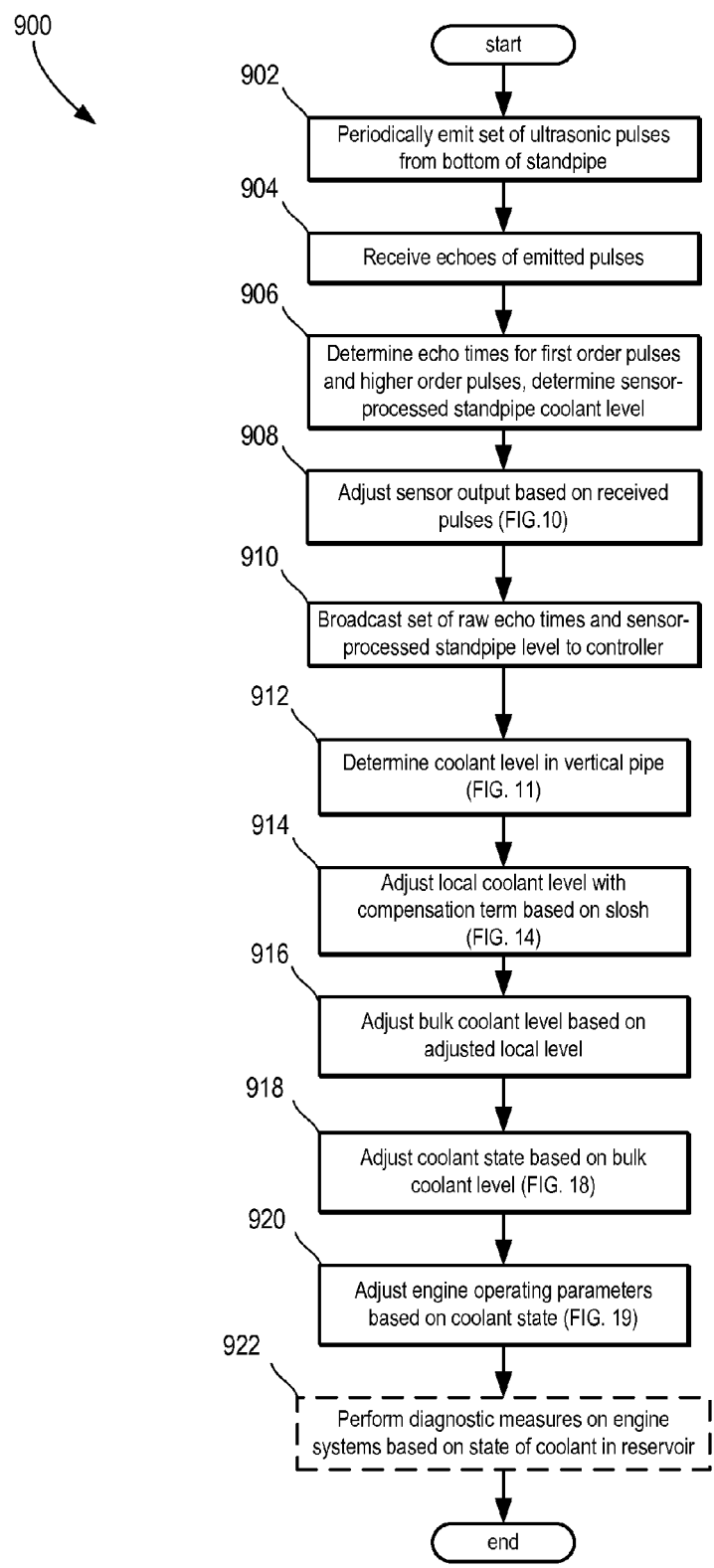
FIG. 9 shows a high-order flowchart for estimating a level of fluid in the coolant reservoir.

FIG. 9 provides a high-level routine 900 for determining a bulk coolant level in a degas bottle based on a level sensor reading in a fluidly coupled vertical standpipe, such as degas bottle 308 and vertical standpipe 310. The routine further depicts the adjusting of engine parameters based on the bulk coolant level. Routine 900 may be executed continuously throughout engine operation to ensure that there is a sufficient level of coolant in the coolant system to prevent overheating of any engine components. Each iteration of routine 900 may be herein referred to as a measurement period. The routine consists of estimating a coolant level in the vertical standpipe based on data from the ultrasonic level sensor, adjusting the estimate of the coolant level in the vertical standpipe based on slosh parameters such as vehicle acceleration, vehicle attitude, and previous coolant levels to determine a current coolant level in the degas bottle, adjusting a long-term bulk coolant level based on the estimate of the current level in the degas bottle, and adjusting engine operating parameters based on the long-term bulk coolant level.

Routine 900 begins at 902, where an ultrasonic level sensor may periodically emit a set of ultrasonic pulses upward from the bottom of the vertical standpipe. For example, as described above, a ULS may emit a set of 5 sequential ultrasonic pulses of a specified energy, each pulse spaced 5-8 milliseconds apart. The energy of the emitted pulses may be determined based on several factors including feedback from the energy of previously-received pulses. Specifically, the energy of the pulses may be increased if previous returning pulses were below a threshold amount of energy, or were not detected, and may be decreased if more than a threshold number of second and/or third-order harmonic echoes were detected. The time interval between each pulse set may be determined based on the expected values of the fluid's speed of sound and total length of standpipe to be measured, such that the time between is at least longer than the period of the first harmonic of the pipe/fluid. For example, the ULS may emit a set of pulses every 100 milliseconds.

Once an ultrasonic pulse is emitted from the ULS, it may travel upward through the coolant in the standpipe until reaching a medium interface, such as a coolant-air interface, or an air-solid interface if the standpipe has no coolant in it. Some of the energy associated with the ultrasonic pulse may be reflected at the interface, creating an echo pulse, and the rest of the energy associated with the ultrasonic pulse may transmit or refract through the interface, or dissipate in some other way. The echo pulse may travel back toward the ultrasonic level sensor, and at 904, may be detected by the ultrasonic sensor. This echo may be referred to as a first-order echo. In some examples, an echo pulse may be at or below a lower threshold energy, and as such may be undetectable by the sensor. In further examples, the echo received by the ultrasonic level sensor may be a second echo associated with an emitted pulse. Each echo that is detected may be assigned a timestamp, as described in further detail below.

When multiple successive echoes are returned with sufficient energy, the associated timestamps may be compared for the primary, secondary and tertiary echoes in comparison to one another and in comparison to multiples for the primary echo. These echoes correlate with the expected harmonic response. These timestamps are provided with sufficient time resolution for proper signal analysis, and indicate the amount of time elapsed between the emission and reception of said echo. This timestamp may herein also be referred to as an echo time. In some examples, a timestamp may only be assigned to pulses with an energy at or above a lower threshold energy. If a single ULS is configured to both send and receive signals within the standpipe, the sensor may be configured to ignore received pulses for a threshold duration after the emitted excitation is stopped. This threshold duration may herein be referred to as a "blanking time" which correlates to a potential reflection that can occur at the bottom of the fluid interface and give a false indication of low fluid level. The blanking time may be determined based on a variety of factors such as the sensor housing materials used, coupling materials assisting to transmit from the transducer to the housing, and other geometric features present in the standpipe. The internal computer or processor of the ULS circuit board may also designate echoes as being first-order echoes or higher-order echoes such as second-order echoes.

At 906, the internal computer of the ULS may determine an echo time for each received pulse. Based on these echo times, the ULS computer may also determine an internal estimate for the local coolant level in the standpipe. The internal coolant height estimate may be based on an estimated speed of sound in coolant, including a temperature compensation factor and an echo time. A coolant level may be estimated for each received first-order echo in a measurement period. An average of the coolant levels in a given measurement period may be determined to reach a final sensor-processed local coolant level in the vertical standpipe. A comparison is made between these signals to ensure the signal is a true detection of the fluid level. During conditions wherein excessive fluid churning or intra-pulse fluid-air movement could be confused with less accurate readings, more complex statistical determinations than an arithmetic mean may be necessary to analyze the timestamps of the first-order echoes. Thus, determining an average may consist of one or more of determining a mean, mode, median, weighted average, other statistical function, and a standard deviation, and then processing the coolant levels using an appropriate mean or median based on data sample outliers. For example, when the primary echo times within the set of pulses are all within 1 microsecond of one another, a high quality signal may be indicated. However, when one primary echo time is significantly different than the other, a lower level of confidence may be indicated.

At 908, an amount of power supplied to the ULS for pulse emission may be adjusted based on one or more of the energies and number of first and second echo times pulses for the current measurement period. In one example, routine 1000 (at FIG. 10) may be executed to adjust the supply of power. Adjusting the power supplied to the ULS for pulse emission may include selectively increasing the power when a first threshold number of received pulses are below a lower threshold energy, and selectively decreasing the power when a second threshold number of higher-order echoes are received in the measurement period. The threshold number of received pulses may be based on the presence of any primary echo data (e.g., the threshold number may be the size of the pulse set) while the threshold number of higher-order echoes may be based on the second order echo times available. Adjusting the power supplied to the ULS is further described below with reference to FIG. 10.

The ULS may broadcast information associated with the emitted and received pulses of the current measurement period to the engine controller (such as controller 12) at 910. For example, the ULS may broadcast a number of received echoes above the lower threshold energy, a sensor-processed local coolant level estimate, timestamps for first and second-order echoes of each emitted pulse in the measurement period, and sensor circuit and standpipe coolant temperature estimates. The ULS circuit board temperature and standpipe coolant temperature estimates may be determined via sensors 367 and 369, respectively. The engine controller may then determine a coolant level in the vertical pipe based on this information. The coolant level in the vertical pipe may herein be referred to as a local coolant level or a local level. Determining a local coolant level may include applying the sensor-processed local coolant level estimate as the local coolant level estimate, or alternatively may include calculating a level based on echo times, a blanking distance, and the physical extent of the standpipe. Determining a local coolant level is described in further detail with reference to FIG. 11.

The coolant level in the standpipe may not correspond directly to the coolant level in the degas bottle, the latter level herein also referred to as the bulk coolant level or bulk level. For example, if the vehicle is accelerating or decelerating, or is at an attitude, the local coolant level may diverge from the bulk coolant level due to slosh. To accommodate for the divergence of the bulk level from the local level due to slosh, a compensation term may be calculated by the engine controller. This compensation term may be used to adjust the local coolant level estimate to a bulk coolant level estimate at 914, for example via routine 1400 at FIG. 14. The compensation term may be based on motion parameters of the vehicle, for example based on one or more of longitudinal attitude and acceleration, lateral attitude and acceleration. Applying compensation to the local coolant level estimate to adjust for slosh is described in further detail in reference to FIG. 14.

After an adjusted local coolant level estimate has been determined for the measurement period at 914, routine 900 proceeds to 916, where the bulk coolant level estimate may be adjusted based on the adjusted local coolant level estimate. Adjusting the bulk coolant level estimate may involve filtering the adjusted local coolant level estimate into the bulk coolant level estimate. Adjusting the bulk coolant level estimate is described in further detail below, in reference to FIGS. 14 and 16. The bulk coolant level estimate may not be adjusted during measurement periods in which a local coolant level estimate is not determined. A bulk coolant level estimate may correspond with one or more bulk coolant states, the bulk coolant states defined by one or more level thresholds.

Routine 900 then proceeds to 918, where the coolant state of the vehicle may be adjusted based on the bulk coolant level estimate. The vehicle may have a fixed number of possible coolant states, for instance, EMPTY, LOW, OK, FAULTED, and UNKNOWN/DEGRADED. Coolant states may correspond directly to a bulk coolant level, or may indicate degradation of hardware components such as an ultrasonic level sensor. In some cases, adjusting the coolant state may occur only a coolant level indicating a new coolant state has persisted for a threshold duration.

Based on the coolant state, engine operating parameters may be adjusted at 920. For example, when the coolant level is below a lower threshold for more than a threshold duration and vehicle operating parameters suggest a proper coolant level can be detected, a low coolant state may be assumed.

This may result in limiting operation where engine loads may be restricted to be below an upper threshold to ensure that engine components will maintain intended operation. In another example, if the coolant state is LOW, the controller may display a message to the engine operator indicating a low coolant level. Adjusting the coolant state is described in further detail with reference to FIG. 18. In some cases, system diagnostics may be executed based on coolant state at 922, for instance, sensor degradation may be determined based on the coolant state and change in coolant state over a duration of vehicle operation. Routine 900 then terminates.

Figure 10:
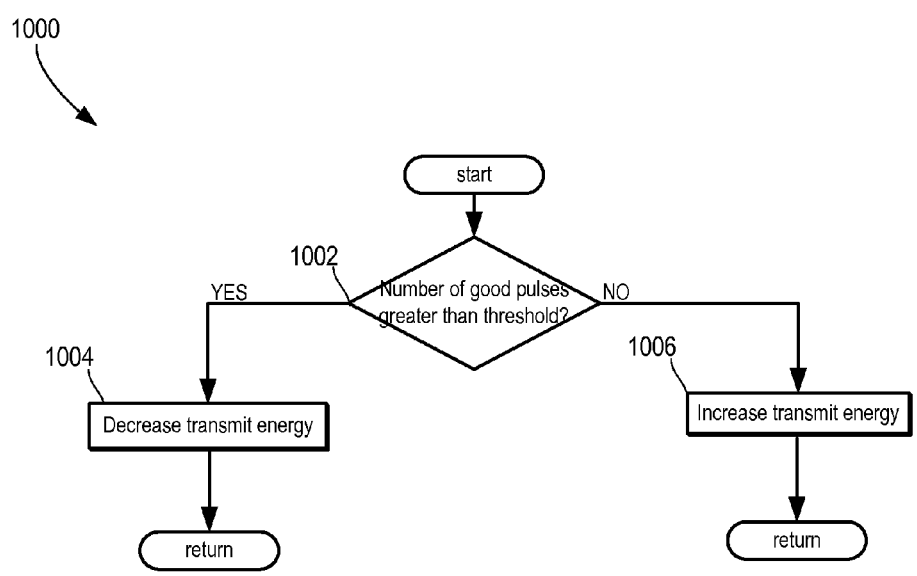
FIG. 10 depicts an example method for adjusting the amount of power supplied to an ultrasonic level sensor in a vertical standpipe of a cooling system.

FIG. 10 depicts a routine 1000 for adjusting the power supplied to the ultrasonic level sensor for pulse emission based on feedback from the energy of received pulses. The power supplied to the ultrasonic level sensor for pulse emission may herein also be referred to as the transmit energy. Routine 1000 may be executed during each measurement period, after the set of pulses has been received, and may increase the energy efficiency of the ultrasonic level sensor.

Routine 1000 begins at 1002, where the number of first-order echoes within the measurement set with an amount of energy above a lower threshold is determined and compared to a threshold number. The lower energy threshold may be determined based a fixed minimum value. This minimum threshold number may be determined based on providing sufficient function under most steady state operation conditions. For example, if 5 pulses were emitted for the measurement period, a threshold number may be 4 pulses out of 5 having an amount of energy above the lower threshold. If the number of echoes with sufficient energy is higher than a threshold, it may be determined that the energy output of the sensor is sufficiently high. In addition, it may be determined that further optimization of the energy output may be possible. In particular, if the energy output is sufficiently high then the energy output of the sensor may be reduced without incurring a substantial drop in the number of echoes with sufficient energy. By reducing the energy output without affecting echo efficiency, power reduction benefits can be achieved. Additionally, when operating with high pulse emission energies, unexpected additional pulses may be detected due to improperly reflected energy that result in false data being provided to the measurement system. Thus, it is beneficial to provide reduced ultrasonic energy whenever conditions allow.

In one example, in response to a low enough number of valid first harmonic echoes (e.g., 0 or 1) being received, energy output level may be increased to attempt to get enough energy quickly to regain sufficient $1^{st}/2^{nd}$ order returns (e.g., a 10%-20% increase). In another example, when all of the first order harmonics are present and more than a high number of second harmonics are validly returned (e.g., more than 4 or 5 second harmonics), the amount of pulse energy broadcast is reduced by a small decrement amount (e.g., a 1% decrease). In other examples, some conditions may indicate maintaining the current transmit energy when all the transmitted pulses are providing clear first and second echo times.

Accordingly, if the number of echoes with an amount of energy above the lower energy threshold is at or above the threshold number, routine 1000 proceeds to 1004, where the energy supplied to the ULS for emitting pulses may be decreased. Otherwise, if the number of echoes with an amount of energy above the lower threshold is below the threshold number, routine 1000 proceeds to 1006, where the energy supplied to the ULS for emitting pulses may be increased. Herein, based on the number of echoes with sufficient energy been lower than the threshold, it may be determined that the energy output of the sensor is not high enough. In addition, it may be determined that further optimization of the energy output is necessary. Accordingly, to improve the number of echoes that have sufficient energy, the energy output of the ULS is increased.

Decreasing transmit energy at 1004 may include, under a first set of conditions, decreasing the transmit energy at a first rate, and under a second set of conditions, decreasing the transmit energy at a second rate, the second rate less rapid than the first rate. For example, the first set of conditions may include receiving a threshold number first-order echoes above the lower energy threshold, while also receiving a number of higher-order pulses above an upper threshold number. In this example, the transmit energy may be decreased at a first slow rate, the rate intended to ensure a continuity of the signals coming back and having a controlled reduction of power. An excessive reduction rate may result in a dithering of sufficient and insufficient data in alternating cycles. This dithering behavior may then be falsely detected a loss of proper signal function resulting in unnecessary vehicle response conditions. The second set of conditions may include every first-order echo in the measurement period being above the lower threshold energy, and a number of higher-order pulses below the upper threshold number. In this example, the transmit energy may be decreased at a second slow rate, the second rate slower than the first. In another example, the first set of conditions may include the transmit energy being at the physical maximum level and the number of first-order echoes above the lower threshold energy is above the threshold number. In comparison, the second set of conditions may include the transmit energy being at the physical maximum level and the number of first-order echoes above the lower threshold energy being below the threshold number.

Increasing the transmit energy at 1006 may include, under a first set of conditions, increasing the transmit energy at a first rate, under a second set of conditions, increasing the transmit energy at a second rate, the second rate less rapid than the first rate. In some examples, under a third set of conditions, the transmit energy may be jumped to the physical maximum level and maintained at the physical maximum level until these conditions are no longer detected. For example, the first set of conditions may include the number of first-order echoes with an amount of energy above the lower energy threshold being below a lower number threshold but non-zero. In this example, the transmit energy may be increased at a faster rate, the rate determined based on the number of valid first order pulse returns lower than a threshold (e.g., the threshold may be 3 pulses). The second set of conditions may include having a low number of second order harmonic pulse returns (e.g., less than 3), in which case the transmit energy may be increased at a lower rate, the rate determined based on the balance of valid first and second harmonic pulse returns. The third set of conditions may include the number of first-order echoes with an amount of energy above the lower energy threshold being zero. In this example, the transmit energy may be increased to a maximum level. In some examples, if one of the first or second set of conditions is detected but the transmit energy is at an upper threshold, the upper threshold below the maximum level, the transmit energy may be maintained and not increased. In another example, transmit energy may be maintained when one of the first or second set of conditions is detected but the transmit energy is above the upper threshold and below the maximum level.

Figure 11:
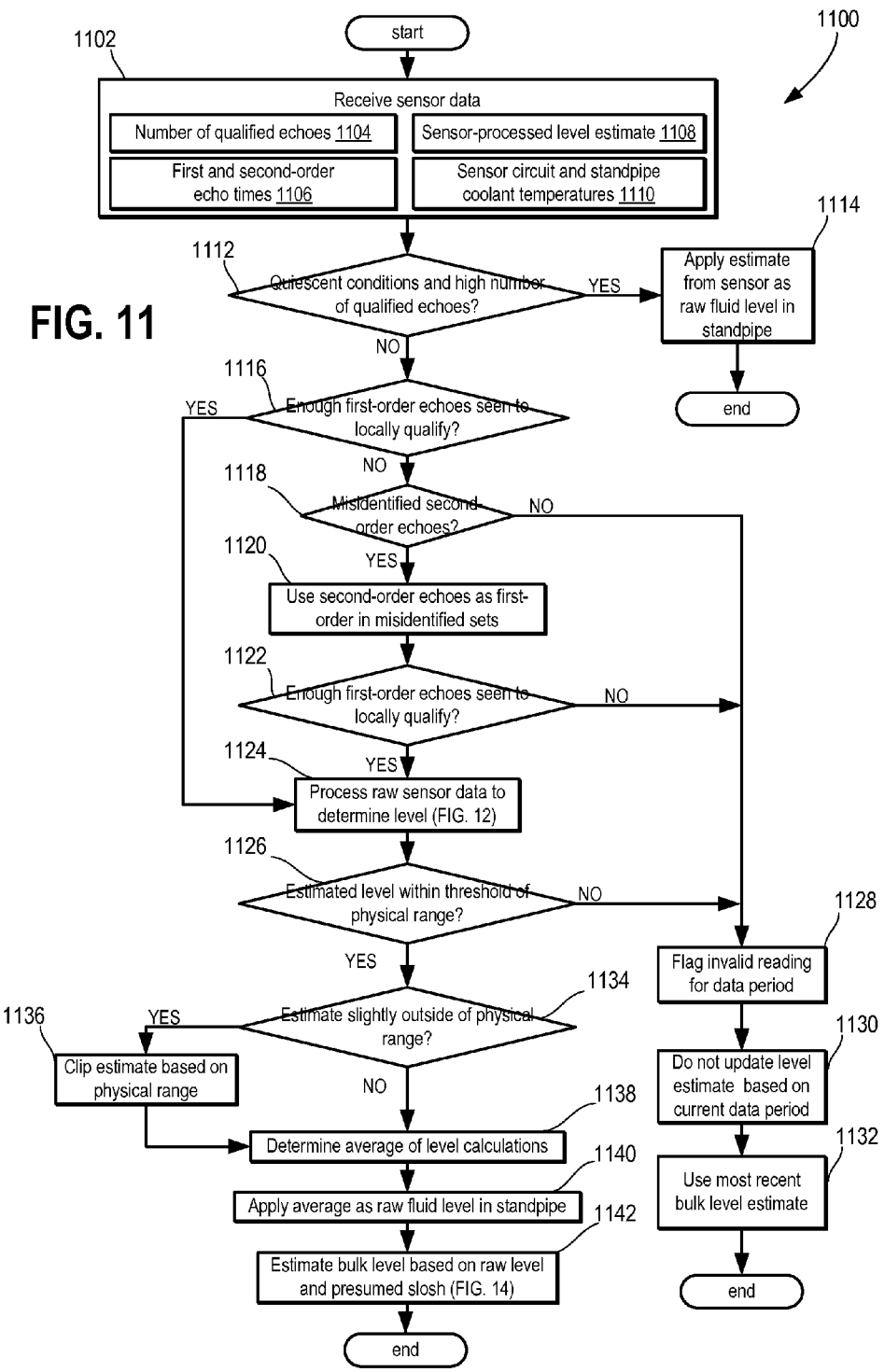
FIG. 11 depicts an example method for estimating a fluid level in a vertical standpipe based on information from an ultrasonic level sensor.

FIG. 11 provides an example routine 1100 for estimating the local coolant level in the standpipe based on information from the ultrasonic level sensor and engine operating conditions, and adjusting this estimate with a compensation term. During a first set of conditions, a local coolant level estimate may be calculated based on a sensor-processed level estimate, and during a second set of conditions, the controller may calculate a level estimate based on one or more of the first-order echo time stamps, estimates of coolant and ULS circuit temperatures, an estimated coolant blend, vehicle acceleration and attitude measurements, and physical parameters of the standpipe. Routine 1100 may be executed during each measurement period.

At 1102, the controller receives raw data from the ultrasonic level sensor, including but not limited to a number of echoes above a lower threshold energy at 1104, echo time-stamps 1106 for both first-order and higher-order echoes, and coolant temperature and ULS circuit board temperature estimates 1110, in addition to receiving a sensor-processed coolant level estimate 1108. At 1112, the engine may determine whether engine conditions are quiescent, and if they are, may apply the sensor-processed coolant level estimate 1108 as the raw fluid level in the standpipe at 1114. Determining whether engine conditions are quiescent may include determining whether one or more of dynamic acceleration of the vehicle, grade/pitch of the vehicle, and/or engine speed change by more than threshold amounts. These parameters may be determined based on information from vehicle accelerometers (e.g., from roll-stability or air bag modules) as well as engine operating parameters from a powertrain/engine control module.

If engine conditions are not determined to be quiescent at 1112, the controller may proceed to calculate a local coolant level based on echo times 1106 and temperatures 1110. At 1116, the controller checks the number of received first-order echoes that are at or above a threshold amount of energy. In some cases, the threshold amount of energy may be the energy level at which signal can be distinguished from noise. If the number of first-order echoes at or above the threshold amount of energy is above a threshold number of echoes, routine 1100 proceeds to 1124 to calculate a coolant level based on these first-order echo times. The threshold number of echoes may be determined based on data collected for baseline fraction of valid first harmonic echoes seen on flat ground, idle, stationary conditions. For example, if the measuring period comprises 5 emitted pulses, the threshold may be 4.

In some examples, a first-order echo may have been misidentified by the internal processor of the ULS circuit board as being a higher-order echo. Accordingly, at 1118, the controller may check the higher-order echo timestamps and determine whether one or more first-order echoes have been misidentified by the sensor as higher-order echoes. Determining whether a first-order echo has been misidentified may be based on comparing the return timestamps of reported first order echoes to the calculated $2^{nd}$ or $3^{rd}$ order times that could occur (calculated based on the speed of sound and 4 standpipe lengths ($2^{nd}$ order) or 6 standpipe lengths (3rd order)). If no first-order echoes were misidentified, then the number of first-order echoes is still below the threshold number. In this case, the controller may flag an invalid reading for the measurement period at 1128 because there are not enough data points to make a reliable estimate of the coolant level in the standpipe. Flagging an invalid measurement period also includes not updating the bulk coolant level based on data from the current measurement period at 1130, and using bulk level data from the most recent valid measurement period at 1132.

If it is determined at 1118 that one or more first-order echoes were misidentified as higher-order echoes, these echoes may be reassigned as first-order echoes at 1120. The controller may then again check whether the number of first-order echoes at or above the threshold amount of energy is above the threshold number of echoes. If the number is still below the threshold number, routine 1100 may proceed to 1128, 1130, 1132 as described above. If the number is at or above the threshold number, routine 1100 continues to 1124, where a local coolant level estimate may be determined, for example via routine 1200 at FIG. 12.

Figure 12:
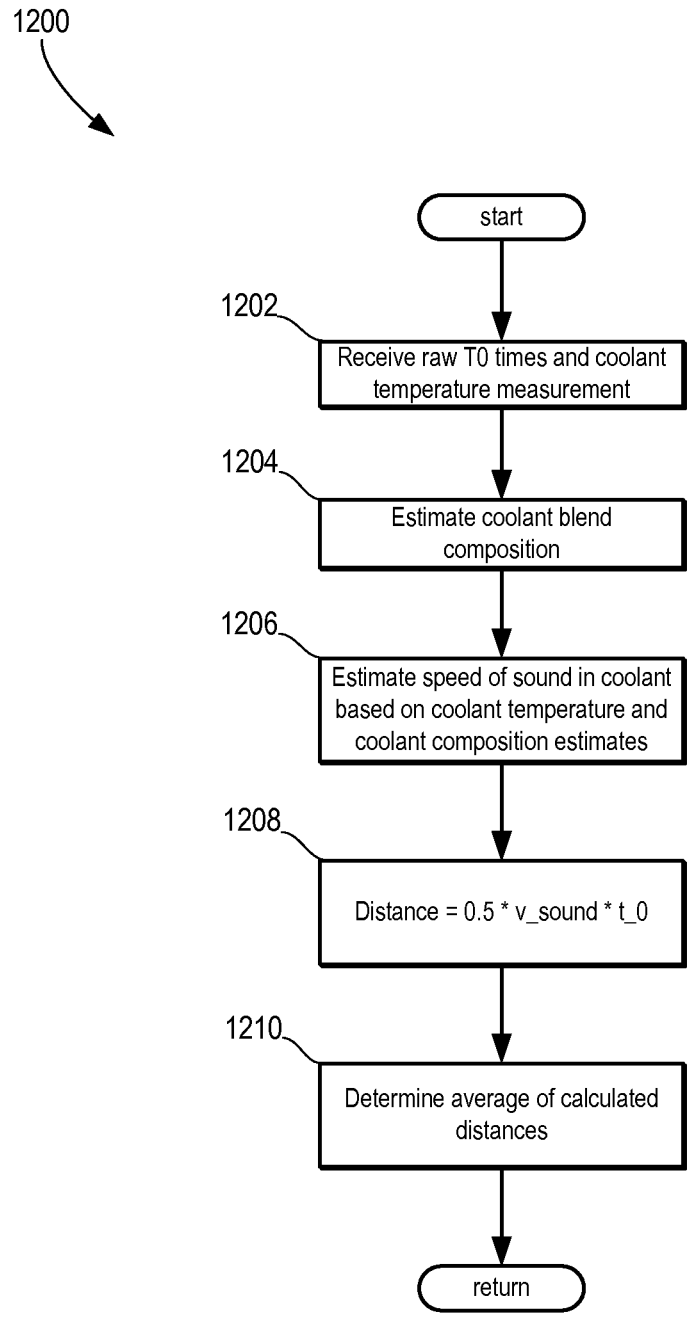
FIG. 12 depicts an example method for estimating a fluid level in a vertical standpipe based on echo times and a fluid composition estimate.

Turning briefly to FIG. 12, routine 1200 provides an example routine for calculating a local coolant level estimate based on echo times and a number of temperature estimates. The calculation is based on the assumption that an ultrasonic pulse travels from the sensor, toward a coolant-air medium interface, and back to the ultrasonic level sensor in the time indicated by its respective timestamp. An estimate of the distance traveled by the ultrasonic pulse is calculated based on the echo time and an estimate of the speed of sound in the coolant.

Routine 1200 begins at 1202, where raw first-order echo times and coolant temperatures are received by the controller. At 1204, a coolant blend composition may be estimated based on comparing a speed of sound estimate (estimated based on an average local standpipe level on flat ground) to a currently measured speed of sound. An estimate for the speed of sound in the coolant may then be determined at 1206, based on estimated coolant and ULS circuit temperatures, as well as the estimated coolant blend. With an estimated speed of sound and a time stamp, a distance traveled for each pulse may be calculated at 1208 based on the formula:

$$Distance = 0.5 * v\_sound * t\_0,$$

where v_sound is the estimated speed of sound, t_0 is the first-order echo time, and the product of these two is multiplied by one half to account for the fact that a pulse must travel twice the length of the coolant level to return to the sensor. A distance may be estimated for each first-order echo in the set that is above the lower threshold energy.

Returning to FIG. 11 at 1126, the standpipe coolant level estimates of routine 1200 may be compared to the physical range of the standpipe. For example, the memory of the controller may contain an upper threshold value for a maximum level of coolant level based on the distance between the ULS sensor and the top of the vertical sensor, and may contain a lower threshold value for a minimum level of coolant based on the distance between the ULS sensor and the lower level sensor hose (316 in FIG. 3). In other examples, the lower threshold value may be based on the blanking distance of the sensor. The physical range of the standpipe may then be any level between the upper physical threshold and the lower physical threshold. If the local level estimates are not within the physical range of the standpipe, routine 1100 proceeds to 1128. In some examples, being within the physical range of the standpipe may include being within a threshold margin below the lower physical threshold or within a threshold margin above the upper physical threshold. In these examples, the threshold margins may be determined based on expected worst-case part tolerances, and further based on the lower and upper physical thresholds themselves.

However, if the estimated standpipe levels are within the physical range of the standpipe, routine 1100 continues to 1134, where a decision is made based on whether the estimated standpipe levels are within the standpipe range, or within the threshold margins outside the raw standpipe. If the raw standpipe level is outside the standpipe range and within the threshold margins, the raw standpipe level is clipped to be within the physical range at 1136. If the raw standpipe level is within the physical range at 1134, clipping may not be necessary, and routine 1100 may continue at 1138.

At 1138 an average of the calculated and clipped level estimates may be determined. Determining an average may consist of one or more of checking a mean, median, and a standard deviation, then processing the coolant levels using an appropriate mean or median based on data sample outliers. For example, when one or more of the samples is outside of the physical range, determining an average may include only the points that were measured as originally in-range. This average may be applied as the raw local coolant level estimate or raw standpipe coolant level estimate for the measurement period. This average may then be applied as the raw standpipe coolant level estimate at 1140. At 1142, a separate routine may be executed to estimate the bulk coolant level based on the raw standpipe coolant level estimate and other factors such as vehicle acceleration and attitude. For example routine 1400 at FIG. 14 may be executed to estimate a bulk coolant level. This process described in further detail with reference to FIGS. 13-16.

FIGS. 13A-13C provide depictions of a coolant reservoir (degas bottle 1302) fluidly coupled to a vertical standpipe 1304, and oriented at three different angles relative to a level plane. Degas bottle 1302 is shown with degas bottle cap 1328. An upper fluidic connection is established between degas bottle 1302 and vertical standpipe 1304 via upper level sensor hose 1326, and may allow a transfer of air between the top of degas bottle 1302 and the top of vertical standpipe 1304. When degas bottle 1302 and vertical standpipe 1304 are level, upper level sensor hose 1326 may extend horizontally between the two vessels, such as illustrated in FIG. 13A. A lower fluidic connection is established between degas bottle 1302 and vertical standpipe 1304 via lower level sensor hose 1318, and may allow a transferring of coolant 1306 between degas bottle 1302 and vertical standpipe 1304. Lower level sensor hose is coupled to degas bottle outlet hose 1316 via a T-joint 1320, oriented so that lower level sensor hose 1318 diverges from outlet hose 1316 in a downward direction. Lower level sensor hose 1318 is coupled to degas bottle outlet 1316 below the bottom of degas bottle 1302, and upstream of turbo outlet 1322. Vertical standpipe 1304 may include ULS 1308 for estimating a local coolant level. ULS 1308 may be connected to a controller area network (not pictured).

By establishing a fluidic connection between a larger vessel, such as degas bottle 1302, and a smaller, narrow vessel such as vertical standpipe 1304, a transfer of fluid between the two vessels produces a greater effect on the coolant level of the smaller vessel than on the larger vessel. During some conditions, local coolant level 1314 and bulk coolant level 1312 may be the same or at least within a lower threshold value of each other, such as illustrated at FIG. 13A. Conditions in which local coolant level 1314 and bulk coolant level 1312 are within a lower threshold value of each other may include when the vehicle is not accelerating and when the vehicle has a level attitude. During other conditions, a fluid transfer between degas bottle 1302 and vertical standpipe 1304 may cause local coolant level 1314 to be greater than bulk coolant level 1312 by at least a threshold amount. Example conditions which may induce such a fluid transfer may include when the vehicle is decelerating and when the vehicle has a nose-down attitude in the embodiment where the standpipe is forward of the degas bottle in the vehicle.

During still other conditions, a fluid transfer between degas bottle 1302 and vertical standpipe 1304 may cause local coolant level 1314 to be less than bulk coolant level 1302 by at least a threshold amount. Example conditions which may induce such a fluid transfer may include when the vehicle is accelerating and when the vehicle has a nose-up attitude in the embodiment where the standpipe is located forward of the degas bottle in the vehicle.

Figure 14:
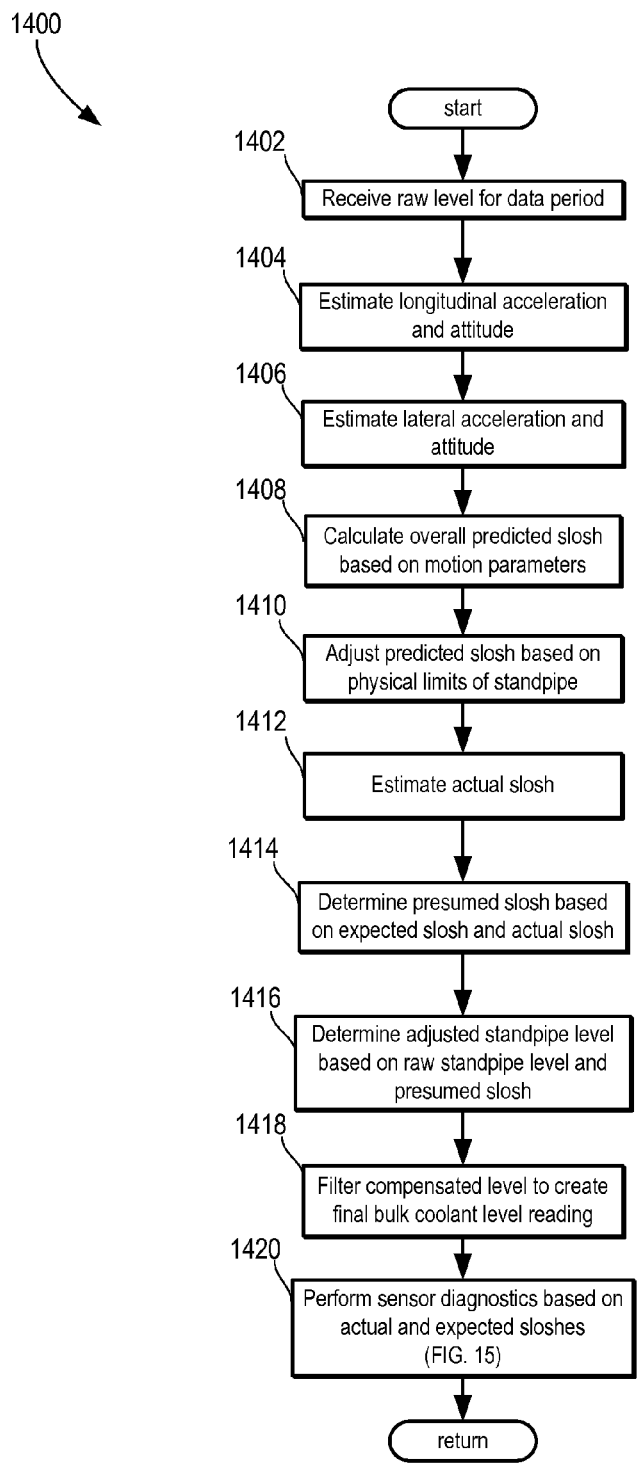
FIG. 14 depicts an example method for determining a slosh term and adjusting a standpipe fluid level estimate based on the slosh term.

In order to adjust an estimate of the local coolant level to an estimate of the bulk coolant level, vehicle acceleration and attitude estimates may be used to estimate the direction and magnitude of the difference in coolant levels, for example via routine 1400 at FIG. 14. Adjusting the local coolant level to reflect the bulk coolant level includes determining a compensation term as an estimate of the divergence between the local standpipe level and the bulk coolant level. This compensation term may herein be referred to as a slosh or a slosh term. The slosh term may have an associated sign and magnitude, and may be added to the raw standpipe level to form an adjusted standpipe level estimate. That is, the slosh term may subtract from or add to the raw standpipe level to form the adjusted standpipe level estimate, which estimates what the standpipe level would be if the vehicle were level and the standpipe and bulk levels were at equilibrium. Therefore, the adjusted standpipe level serves as an instantaneous estimate of the coolant level in the degas bottle. The bulk coolant level estimate may then be updated based on the adjusted standpipe level estimate. Executing routine 1400 during a measurement period may be based on whether a valid coolant level reading exists for the measurement period. For example, routine 1400 may be executed during measurement periods in which a raw standpipe coolant level has been determined, and may not be executed during measurement periods wherein the coolant level readings have been flagged as invalid, such as at 1128 in routine 1100.

Routine 1400 begins at 1402, where the engine controller receives a raw local coolant level estimate for the current measurement period. The raw local coolant level estimate may be determined by a separate routine such as routine 1100 at FIG. 11. The raw level estimate is used later in routine 1400, in combination with a slosh term, to determine a bulk coolant level estimate. After receiving the raw coolant level estimate, routine 1400 proceeds to 1404, where estimates of longitudinal acceleration and longitudinal attitude may be determined. Longitudinal acceleration estimates may be based on data from an accelerometer, or alternatively from a time derivative of velocity sensor measurements. Longitudinal attitude estimates may be based on data from various sensors. Similarly, at 1406, the controller may determine estimates for the lateral acceleration and lateral attitude of the vehicle. Lateral acceleration estimates may be based on data from an accelerometer, or alternatively may be calculated from velocity and wheel speed measurements. Lateral attitude estimates may be based on data from various sensors.

Based on the estimates of acceleration and attitude in both the longitudinal and lateral directions made at 1404 and 1406, an expected or predicted slosh term may be determined via a transfer function. In one example, the transfer function may be expressed by the following equation:

$$\text{Expected Slosh} = (\text{Long. Gain})*[(\text{Long. Acc. \%})* (\text{Long. Acc.}) + (1 - \text{Long. Acc. \%})*(\text{Long. Att.})] + (\text{Lat. Gain})*[(\text{Lat. Acc. \%})*(\text{Lat. Accel.}) + (1 - \text{Lat. Acc. \%})*(\text{Lat. Att.})],$$

where Long. Gain and Lat. Gain are weighting factors for the longitudinal and lateral slosh estimates, Long. Acc. % and Lat. Acc. % are weighting factors which weight the relative contributions of acceleration and attitude in the slosh estimate for each direction, Long. Acc. is an estimated longitudinal acceleration, Long. Att. is an estimated longitudinal attitude, Lat. Acc. is an estimated lateral acceleration, and Lat. Att. is an estimated lateral attitude. Acceleration estimates may be in units of distance per squared unit time, while attitude estimates may be in units of degrees inclination or static grade percent in that axis. The determination of longitudinal and lateral gains may be based on correlation to flat ground non-accelerating data versus tilt table data, or based on vehicle data taken at a span of accelerations and static attitudes, and may respectively be in units of percent contribution of correlation. The relative weighting of acceleration and attitude may be determined based on the same correlation data using a method of data fitting (e.g, least squares estimation).

After determining a predicted slosh term, the adjusted standpipe coolant level estimate (that is, the raw level estimate plus the predicted slosh term) may be above or below the physical range of the standpipe (as earlier described with reference to FIG. 11). In these examples, the predicted slosh may be adjusted based on the physical range of the standpipe. In one example, if the predicted slosh and the raw standpipe level estimate add to be greater than the height of the standpipe, adjusting the predicted slosh based on the physical range of the standpipe may include clipping the predicted slosh so that the adjusted standpipe coolant level estimate is at upper threshold of the physical range. In another example, if the predicted slosh plus the raw standpipe level estimate add to be less than the reservoir height, adjusting the predicted slosh may include clipping the slosh estimate so that the adjusted standpipe coolant level estimate is at the lower threshold of the physical range.

In addition to an expected slosh term, an actual slosh term may be estimated at 1412. An estimate of actual slosh may be determined based on a comparison of the raw standpipe coolant level estimate to a bulk level estimate. In one example, the actual slosh may be the difference between the raw standpipe coolant level in the current measurement period and the most recent bulk level estimate.

Based on a comparison between an expected slosh and an actual slosh, a presumed slosh term may be determined at 1414. In one example, determining a presumed slosh may include, in the signed direction of expected slosh, choosing the lower absolute value of actual slosh and the compensated level as the presumed slosh. This example is further explained below, with reference to FIG. 16. In a further example, if both the unclipped expected slosh and actual slosh are within the physical range of the standpipe and the magnitude of expected slosh is greater than the magnitude of actual slosh, the expected slosh may be clipped based on the actual slosh, then applied as the presumed slosh. This example is further explained below, with reference to FIG. 17.

After determining a presumed slosh for the measurement period, the presumed slosh may be applied to the raw standpipe level estimate at 1416 to determine the adjusted standpipe coolant level estimate. The bulk coolant level estimate may then be updated based on the adjusted standpipe coolant level estimate at 1418. In one example, a filter may be used to integrate the adjusted standpipe coolant level estimate from the current measurement period into the long term bulk coolant level estimate. Filtering the adjusted standpipe level estimate may include filtering through a low-pass filter based on a variable time constant, the time constant determined based on sign and magnitude of difference between the instantaneous slosh compensated reading and the long term bulk level estimate, as well as on the amount of time between last valid reading and current valid and slosh compensated reading. In this way, transient changes in coolant level may be smoothed out, and a steadier estimate of the bulk coolant level may be formed.

Routine 1400 then proceeds to 1420, where sensor diagnostics may be performed based on a comparison of the expected slosh and actual slosh terms for the measurement. In one example, an expected slosh integral and an actual slosh integral may be respectively updated based on the expected slosh and actual slosh terms for the measurement period. These integrals may be incremented whenever an expected slosh or actual slosh is detected, and may be decremented by a fixed amount each measurement period. Sensor degradation may be made based on the ratio of the two integrals, and is further described with reference to FIG. 15.

Figure 15:
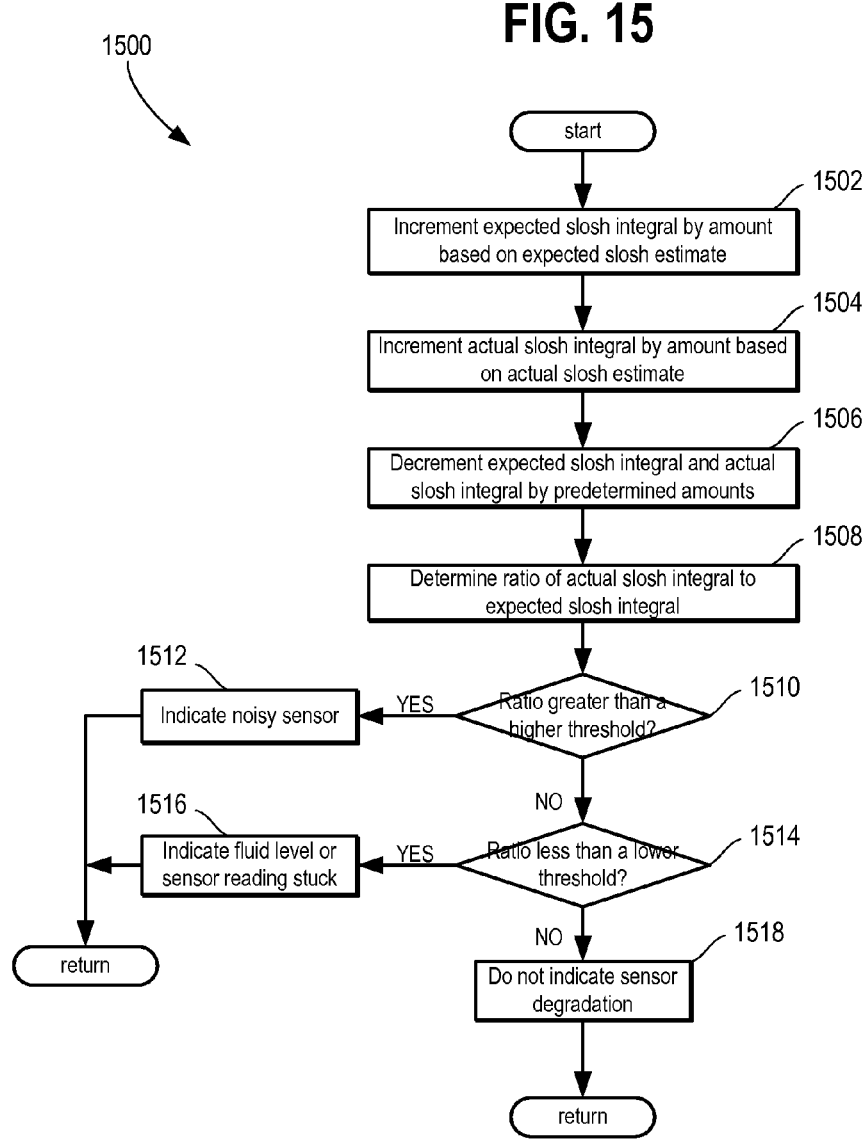
FIG. 15 depicts an example method for detecting degradation of the ultrasonic level sensor based on accumulated slosh terms.

FIG. 15 provides a routine 1500 for determining whether an ultrasonic level sensor in a vertical standpipe (such as ULS 362 of FIG. 3) is degraded. The routine is based on a comparison of amounts of expected slosh and actual slosh accumulated over time. The accumulation of the amounts of expected slosh and actual slosh may be characterized by an expected slosh integral and an actual slosh integral. By comparing these integrals, an engine controller may determine whether more or less slosh than expected has been detected over time, and under some conditions may indicate degradation of the sensor based on this comparison.

Routine 1500 begins at 1502, where the value of the expected slosh integral may be incremented if expected slosh has been detected for the measurement period. For example, motion parameters may indicate an amount of expected slosh at 1408 in FIG. 14, and the expected slosh integral may be incremented by an amount based on the amount of expected slosh in the measurement period. Similarly, if actual slosh has been detected for the measurement period, the value of the actual slosh integral may be incremented at 1504. The amount by which the actual slosh integral is incremented may be based on the amount of actual slosh detected. Based on a comparison of the two integrals, the ultrasonic level sensor may be determined to be degraded due to excessive noise if a first set of conditions is met, and may be determined to be degraded due to a stuck reading if a second set of conditions is met.

At 1506, each of the expected slosh integral and the actual slosh integral may be decremented by a predetermined amount. In one example, each integral may be decremented by the same fixed amount each measurement period, the fixed amount determined based on a baseline amount of integration per loop measured under verified level non-accelerating conditions where there is less than a lower threshold amount of slosh, thereby establishing a base noise level of the calculation. In another example, the actual slosh integral may be decremented by a first fixed amount each measurement period, and the expected slosh integral may be decremented by a second fixed amount each measurement period, the first amount determined based on a baseline amount of integration per loop measured under verified level non-accelerating conditions where there is no or limited slosh, thereby establishing a base noise level of the calculation, and the second amount a smaller fraction (e.g., 80%) of the first amount. In this way, the expectation integral decrement rate is biased toward expecting some amount of slosh during each measurement period. In a further example, each integral may be decremented by the same variable amount each measurement period, the variable amount for each measurement period determined based on the same conditions as above to determine a baseline, and further including varying the decrement rate based on a magnitude of expected slosh, calculated instantaneously based on the weighted combination of longitudinal and lateral acceleration and attitude changes. In a still further example, the expected slosh integral may be decremented by a first variable amount each measurement period, and the actual slosh integral may be decremented by a second variable amount each measurement period, the first and second amounts determined based on the same principles as the other combination examples above. Other possibilities for decrementation may include one integral being decremented by a fixed amount, and the second integral being decremented by a variable amount.

After each integral has been incremented based on the amounts of slosh detected during the measurement period, and decremented based on one of the above example baseline noise compensations above or a similar compensation, a ratio of the actual slosh integral and the expected slosh integral may be determined at 1508. In one example, the actual slosh integral amount may be divided by the expected slosh integral amount, and this number may be applied as the ratio of the two.

At 1510, this ratio is compared to an upper threshold. The upper threshold ratio may be determined based on measuring the largest ratios seen on a test that physically stresses the amount of slosh within the standpipe (e.g., placing a vehicle on a shaker table and operating the table at a variety of amplitudes/frequencies to find worst case in resonance with slosh reading). Alternatively, the upper threshold ratio may be determined based by directly instituting an electrical noise signal on the level sensor input into the electronic control module. The ratio being greater than the upper threshold may indicate that more slosh was detected than was expected by more than a threshold amount. If the ratio is greater than the upper threshold, routine 1500 may proceed to 1512, where the controller may indicate that the ultrasonic level sensor is degraded due to noisiness. After indicating degradation of the sensor due to noisiness, routine 1500 terminates.

If the ratio is not greater than the upper threshold, routine 1500 proceeds to 1514, where the ratio from 1508 may be compared to a lower threshold. The lower threshold may be determined based on performing one or more drive cycles (e.g., one of FTP or US06) take place at a near empty, near full and half full standpipe/degas bottle level on flat ground before each test respectively. These tests include clamping either the upper or lower standpipe hose completely shut as to prevent gas or fluid exchange during the drive cycle. Thus, the lower threshold may represent a baseline level of noise. The lowest ratios seen from these tests are used to set the lower threshold level. The ratio being less than a lower threshold may indicate that less slosh was detected than was expected by more than a threshold amount.

If the ratio is less than the lower threshold, routine 1500 may proceed to 1516, where the controller may indicate that the ultrasonic level sensor may be stuck or that fluid transfer between the degas bottle and the vertical standpipe may be physically impeded. The controller may distinguish between these two degradations based on waiting for both a predetermined period of time or distance traveled before determining if the fault disappeared, thus suggesting the ratio is low due to obstruction. If the ratio is not less than the lower threshold, routine 1500 proceeds to 1518, where sensor degradation is not indicated, and routine 1500 then terminates.

Figure 16:
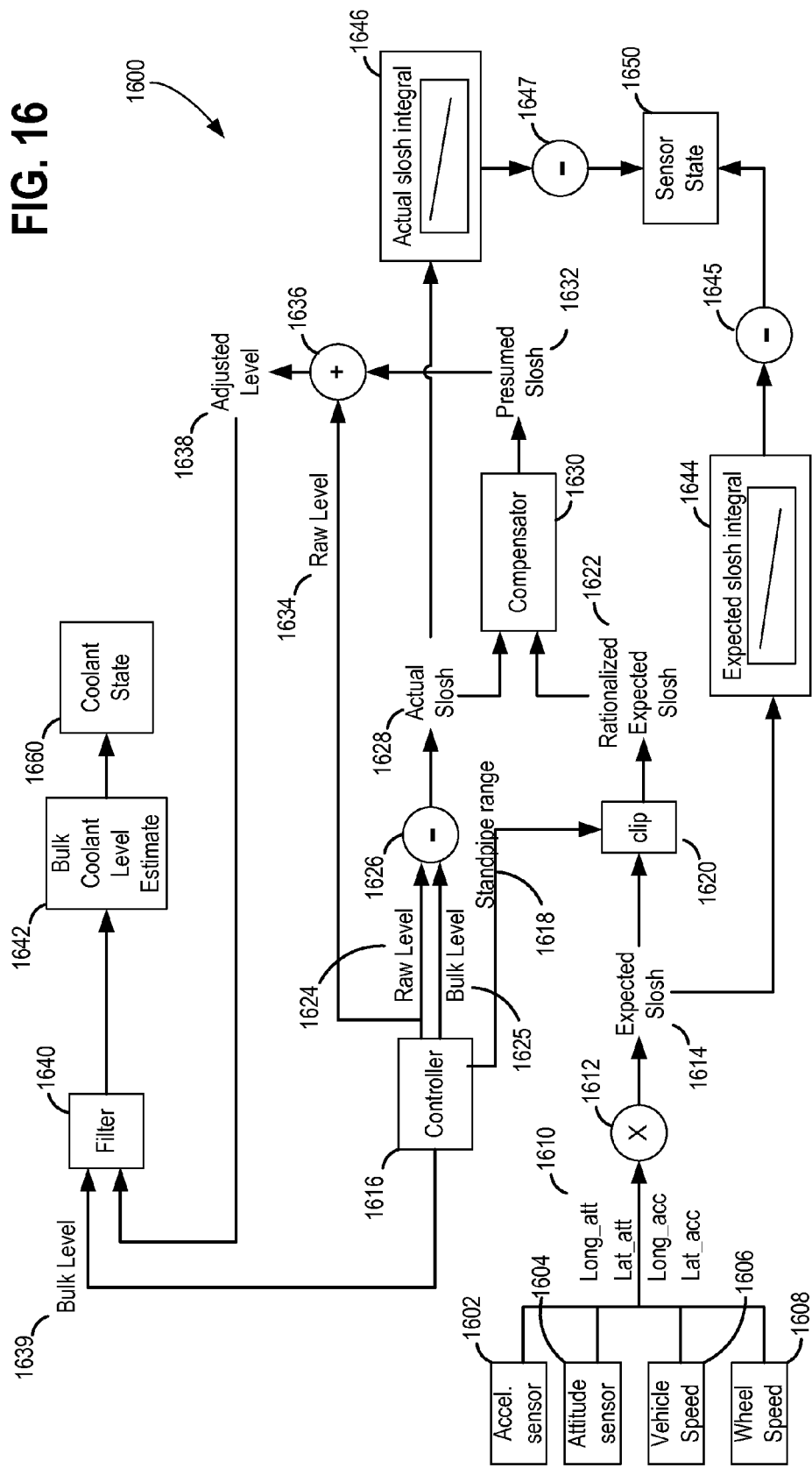
FIG. 16 depicts an example control system for determining a slosh term and adjusting a bulk coolant level estimate based on the slosh term.

FIG. 16 provides a control scheme 1600 for determining an assumed slosh, applying the assumed slosh to the raw standpipe coolant level to determine an adjusted standpipe coolant level, and updating a bulk coolant level based on the adjusted standpipe coolant level. Data from motion sensors such as acceleration sensor 1602, attitude sensor 1604, vehicle speed sensor 1606, and wheel speed sensor 1608 may be used to determine longitudinal acceleration, lateral acceleration, longitudinal attitude, and lateral attitude at 1610. In some examples, both longitudinal and lateral accelerations may be determined based on data from a single acceleration. In other examples, longitudinal and lateral accelerations may be determined from separate acceleration sensors. Similarly, longitudinal and lateral attitudes may be determined by one or more attitude sensors. At 1612, variables 1610 are used as input to a function determining an expected slosh 1614. In one example, function 1612 may be expressed by the equation described above with reference to FIG. 14. Expected slosh 1614 may then be clipped at 1620, and additionally an expected slosh integral 1644 may be incremented based on expected slosh 1614. Expected slosh integral 1644 is described below in further detail. Clip 1620 may be based on the physical range of the standpipe 1618, as described above with reference to FIG. 14, which may be stored in and accessed from the memory of controller 1616. Clipping expected slosh 1614 at 1620 results in a rationalized expected slosh 1622.

In addition to rationalized expected slosh 1622, an actual slosh 1628 may be determined based on the difference 1626 of the raw standpipe coolant level 1624 and the bulk coolant level 1625. Coolant levels 1624 and 1625 may be accessed via controller 1616. Actual slosh integral 1646 may be incremented based on actual slosh 1628. Actual slosh integral is described below in further detail. The rationalized expected slosh 1622 and the actual slosh 1628 may serve as inputs to compensator 1630. Compensator 1630 may determine a presumed slosh 1632 based on inputs 1622 and 1628.

In one example, compensator 1630 may compare sloshes 1622 and 1628, applying rationalized expected slosh 1622 as presumed slosh 1632 under a first set of conditions, and applying actual slosh 1628 as presumed slosh 1632 under a second set of conditions. For instance, the first set of conditions may include sloshes 1622 and 1628 being of the same sign (that is, both estimate a positive amount of slosh or both estimate a negative amount of slosh), and both sloshes being within the physical range of the standpipe 1618, but rationalized expected slosh 1622 being of a lesser magnitude than actual slosh 1628. The second set of conditions may include sloshes 1622 and 1628 being of the same sign, and both sloshes being within the physical range of the standpipe 1618, but actual slosh 1628 being of a lesser magnitude than rationalized expected slosh 1622.

In another example, compensator 1630 may adjust rationalized expected slosh 1622 based on actual slosh 1628, and apply the adjusted amount of slosh as presumed slosh 1632. Adjusting rationalized expected slosh 1622 based on actual slosh 1628 may include, if expected slosh 1622 is greater than actual slosh 1628, applying only a portion of rationalized expected slosh 1622 as presumed slosh 1632. The actual slosh 1628 may be less than the rationalized expected slosh 1622 if fluid exchange between the degas bottle and the standpipe is physically impeded. By applying only a portion of the rationalized expected slosh as the presumed slosh when the rationalized expected slosh is greater than the actual slosh, the accuracy of a bulk coolant level estimate may be improved. If expected slosh 1622 is less than actual slosh 1628, adjusting rationalized expected slosh 1622 based on actual slosh 1628 may include compensating only by the amount expected, the expected amount a conservative amount based on a predetermined mapping of the vehicles propensity to slosh.

Presumed slosh 1632 may be applied to raw standpipe coolant level 1634 to determine adjusted standpipe coolant level 1638. In one example, applying presumed slosh 1632 to raw standpipe coolant level 1634 may involve the addition of presumed slosh 1632 to raw standpipe coolant level 1638. Filter 1640 may update bulk coolant level 1639 (accessible via controller 1616) based on adjusted standpipe coolant level 1638, thereby determining the updated bulk coolant level estimate 1642. Filtering bulk coolant level 1639 based on adjusted standpipe coolant level 1638 may include determining a time constant based on the overall magnitude of slosh compensation being applied to the instantaneous level reading (e.g., more filtering if more compensation applied), and further based on the signed magnitudes of adjusted standpipe coolant level 1638 level reading and bulk coolant level 1639. Coolant state 1660 may then be updated based on updated bulk coolant level estimate 1642, as described in further detail with reference to FIG. 18.

Returning to expected slosh integral 1644, the integral may be incremented based on the magnitude of expected slosh 1614. For example, expected slosh integral 1644 may be incremented by an amount directly proportional to expected slosh 1614. Similarly, actual slosh integral 1646 may be incremented based on the magnitude of actual slosh 1628. Expected slosh integral 1644 and actual slosh integral 1646 may be decremented at 1645 and 1647, respectively. In one example, each integral may be decremented by the same fixed amount each measurement period, the fixed amount determined based on the compensation methods described at 1506 of FIG. 15. After integrals 1644 and 1646 have been decremented at 1645 and 1647, sensor state 1650 may be determined at least in part based on the integrals. In one example, a ratio of actual slosh integral 1646 the actual slosh integral amount may be divided by the expected slosh integral amount, and determining the state of the sensor may be based on a comparison of this ratio to both an upper threshold and a lower threshold.

Figure 17:
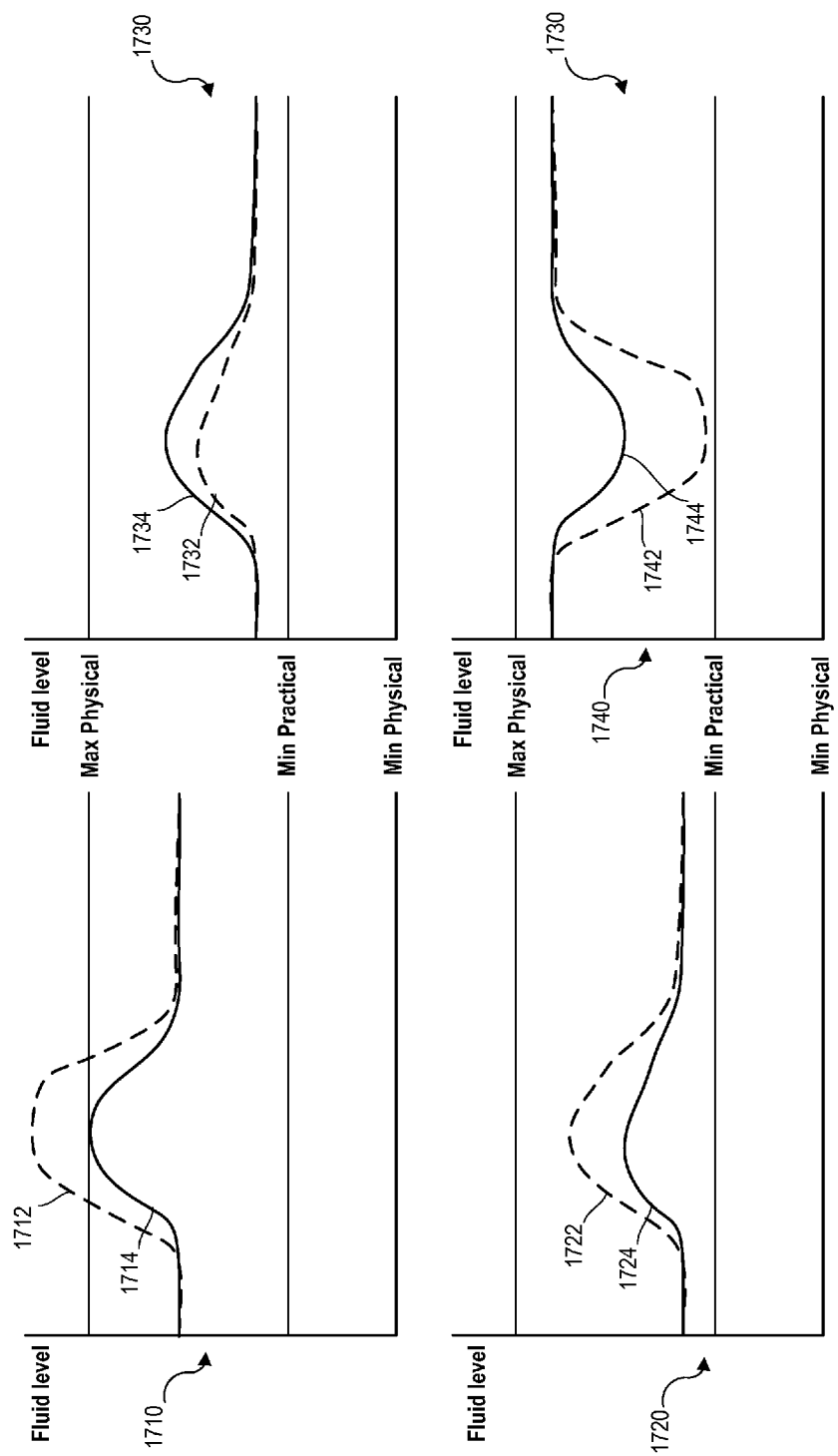
FIG. 17 shows four instances of slosh within a standpipe compared to predicted amounts of slosh.

FIG. 17 provides illustrations of various slosh conditions that compensator 1630 of FIG. 16 may encounter. Plots 1710, 1720, 1730, 1740 show fluid levels based on estimated sloshes (dashed lines) and actual sloshes (solid lines). At 1710, expected slosh 1712 is positive and greater than the maximum physical level of the standpipe, while the actual slosh 1714 is positive and at the maximum physical level of the standpipe. During such a condition, actual slosh 1714 may be applied as the presumed slosh for the measurement period as it may be the case that a temporary obstruction in a hose (e.g., a fluid trap) or the actual end of the vertical standpipe (e.g., due to stackup) has physically limited the slosh amount.

At 1720, both expected slosh 1722 and actual slosh 1724 are positive and within the physical range of the standpipe, and the magnitude of expected slosh 1722 is greater than the magnitude of actual slosh 1724. In such a condition, only a portion of expected slosh may be applied as the presumed slosh for the measurement period.

At 1730, both expected slosh 1732 and actual slosh 1734 are positive, and the magnitude of expected slosh 1732 is less than that of actual slosh 1734. In such a condition, expected slosh 1732 may be applied as the presumed slosh for the measurement period.

At 1740, both expected slosh 1742 and actual slosh 1744 are negative and within the physical range of the standpipe. During such a condition, actual slosh 1744 may be applied as the presumed slosh for the measurement period, as a temporary hose obstruction (e.g., a fluid trap) may be present. By choosing the slosh with the lower magnitude, preventing overcompensation for a model of expected slosh with inaccurate estimates of the gain of acceleration or attitude to slosh, or for a temporarily obstructed hose, may be achieved.

Figure 18:
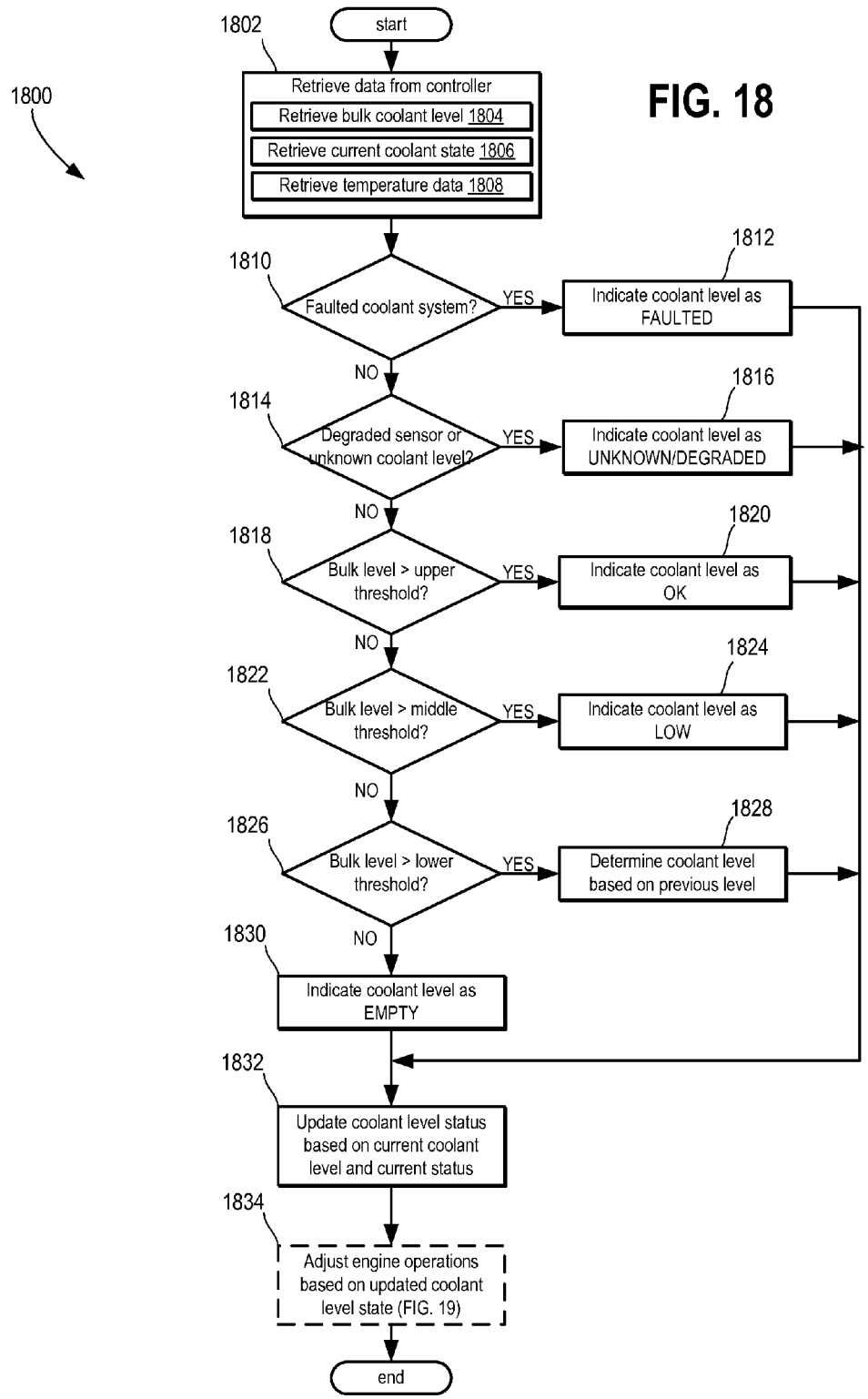
FIG. 18 depicts an example method for determining a coolant level based on comparing a bulk coolant level estimate to various thresholds.

FIG. 18 depicts a routine 1800 for updating a coolant state based on the bulk coolant level estimate and the current coolant state. The updated bulk coolant level estimate may correspond to one or more coolant states. For example, the bulk coolant level estimate may be one of OK, LOW, EMPTY, UNKNOWN/DEGRADED, and FAULTED. In this example, the bulk coolant level estimate may be OK if it is above a higher threshold level, and may be LOW if it is below the higher threshold but above a lower threshold. Additionally, the bulk coolant level estimate may be EMPTY if it is below a lower threshold. Furthermore, a middle threshold may be included, as described below with reference to 1822 and 1826. In some examples, routine 1800 may only update the coolant state if a bulk coolant level estimate corresponding to a different coolant state has persisted for longer than a threshold duration. Routine 1800 may be executed with a coolant system such as that described in FIGS. 2-9, and may be executed during each measurement period in which a valid bulk coolant level estimate is determined, after the bulk coolant level estimate has been updated (such as via routine 1400 or control scheme 1600).

Routine 1800 begins at 1802, where bulk coolant level estimate 1804, current coolant state 1806, and temperature data 1808 are received from an engine controller. At 1810, the controller may determine whether the coolant system is faulted. Conditions that indicate the coolant system being faulted may include a lost connection to the controller area network, zero echoes being received for the measurement period, or an engine temperature being above an upper threshold. If the coolant system is determined to be faulted at 1810, routine 1800 proceeds to 1812, where the controller may indicate that the coolant level is FAULTED. Routine 1800 may then update the coolant state based on the current coolant level and the current coolant state at 1832. If the coolant system is determined to not be faulted 1810, routine 1800 proceeds to 1814.

Continuing at 1814, the controller may determine if the ultrasonic level sensor is degraded or if the coolant level is unknown for the current measurement period. Either condition may correspond to a coolant level of UNKNOWN/DEGRADED. An ultrasonic level sensor may be determined to be degraded if, for example, the engine controller had previously indicated a noisy sensor or a stuck sensor at 1512 or 1516 in routine 1500. Alternatively, sensor degradation may be determined if the expected amount of slosh suggests that the level of vehicle acceleration/attitude occurring instantaneously is too high to compensate for (i.e., if the expected slosh indicates an out of range transient reading). The coolant level may be determined to be UNKNOWN/DEGRADED if, for example, the raw standpipe coolant level estimate had been outside of the physical range of the standpipe by more than a threshold amount, as described with reference to 1126 at FIG. 11, or alternatively if the expected slosh for the measurement period is greater than a threshold magnitude, the threshold magnitude determined based on the expected slosh being more than a percentage of total standpipe height (e.g., plus or minus 25 mm on a 100 mm standpipe). Additionally, the coolant level may be determined to be UNKNOWN if an insufficient number of valid pulse echoes are returned but not for a enough measurement periods to set the coolant level to a detected FAULTED state for the sensor. If the ultrasonic level sensor is determined to be degraded or if the bulk coolant level estimate is determined to be unknown for the measurement period, the controller may indicate that the coolant level is UNKNOWN/DEGRADED at 1816. Routine 1800 may then update the coolant state based on the current coolant level and the current coolant state at 1832, as described below in further detail. Returning to 1814, if conditions do not indicate that the ultrasonic sensor is degraded and bulk coolant level estimate is known, routine 1800 proceeds to 1818.

At 1818, the bulk coolant level estimate is compared to an upper threshold level to determine whether the coolant level is OK. The upper threshold level may be determined based on the pre-determined correlation of the sensor measurement when a vehicle that is stationary on level ground is filled to the lowest acceptable factory-recommended fill level. If the bulk coolant level estimate is above the upper threshold level, the current coolant level may be indicated as OK at 1820. In some examples, the current coolant level may only be indicated as OK if the bulk coolant level estimate is above the upper threshold level by more than a predetermined amount. Routine 1800 may then update the coolant state based on the current coolant level and the current coolant state at 1832, as described below in further detail. Returning to 1818, if the bulk coolant level estimate is not determined to be above the upper threshold level, routine 1800 proceeds to 1822.

At 1822, the bulk coolant level estimate is compared to a middle threshold level to determine whether the coolant level is LOW. Note that at 1822, the bulk coolant level estimate has already been determined to be below the upper threshold level. The middle threshold level may herein also be referred to as the LOW threshold level. If the bulk coolant level estimate is determined to be above the LOW threshold, the coolant level may be indicated to be LOW at 1824. Routine 1800 may then update the coolant state based on the current coolant level and the current coolant state at 1832, as described below in further detail. Returning to 1822, if the bulk coolant level estimate is not determined to be above the middle threshold level, routine 1800 proceeds to 1826.

At 1826, the bulk coolant level estimate is compared to a lower threshold level to determine whether the coolant level is LOW or EMPTY. The lower threshold level may herein also be referred to as the EMPTY threshold level. Note that at 1826, the bulk coolant level estimate has been determined to be below the LOW threshold level. Thus, at 1826 it is determined if the bulk coolant level estimate is between the LOW and EMPTY threshold levels, or if it is below the EMPTY threshold level. If the bulk coolant level estimate is below the EMPTY threshold level, the coolant level is indicated to be EMPTY at 1830. Routine 1800 may then update the coolant state based on the current coolant level and the current coolant state at 1832, as described below in further detail. Returning to 1826, if the bulk coolant level estimate is determined to be above the lower threshold level, routine 1800 proceeds to 1828, where the coolant level is determined based on the coolant state.

Specifically, at 1828 if the bulk coolant level estimate is above the EMPTY threshold level but less than the OK threshold and the coolant state is EMPTY, the controller may indicate that the coolant level is EMPTY. If the bulk coolant level estimate is above the EMPTY threshold and the coolant state is OK, the controller may indicate that the coolant level is OK. In this way, the coolant state may not be changed from EMPTY to LOW until the bulk coolant level estimate is above the OK threshold.

At 1832, the coolant state may be updated based on coolant level. In some examples, the coolant state may only change after a coolant level indicating a new coolant state has persisted for a threshold duration. In this way, by not changing the coolant state based on short-term fluctuations in coolant level about a threshold, the consistency of coolant state may be improved. Because changing a coolant state may include adjusting engine parameters, a consistent coolant state may improve engine operating conditions. In one example, the threshold duration may be based on a threshold number of measurement periods. This threshold duration may differ for each coolant state, or alternatively for each set of coolant states. As a non-limiting example, adjusting the coolant state from OK to LOW may require indicating a LOW bulk coolant level for a different threshold number of measurement periods than adjusting the coolant state from LOW to EMPTY requires indicating an EMPTY bulk coolant level.

In some examples, restrictions may be placed on changing coolant states. For example, the coolant state may only change to EMPTY if the coolant level has been indicated as EMPTY for a first threshold number of measurement periods, not been indicated as being one of LOW or OK for a second threshold number of measurement periods, the second threshold number greater than the first. In this way, transient dips into an EMPTY range may be rejected from falsely detecting EMPTY state. Additionally, the coolant state may only change to EMPTY after the vehicle movement has been detected and the vehicle is determined to be in gear during the current key cycle. In this way, an operator of the vehicle may fill the system with coolant and allow it to move to a detected full OK state without having to continuously reset the control module in order to exit the EMPTY state if that is a requirement.

At 1834, engine operating parameters are adjusted based on the updated coolant state. In some examples, the coolant state may not have been updated for the measurement period, and engine parameters may be maintained from the previous measurement period. However, if the coolant state has been updated, restrictions may be placed on or lifted from engine operating parameters. For example, if the coolant state was updated from OK to EMPTY, commands for engine loads above a threshold load may be disallowed while the coolant state remains EMPTY to prevent overheating of engine components. Adjusting engine operating parameters based on coolant state is described in further detail below, with reference to FIG. 19. Routine 1800 then terminates.

Figure 19:
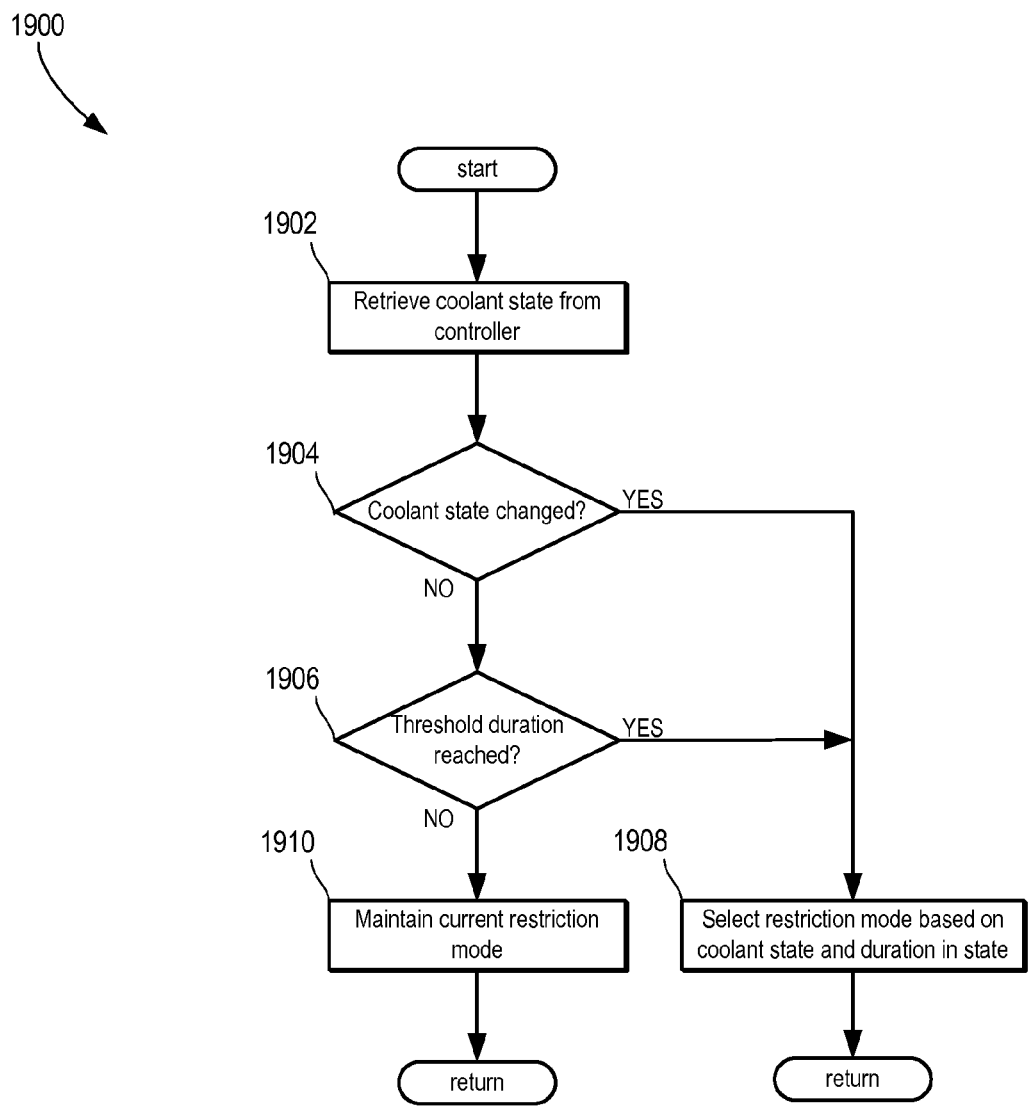
FIG. 19 depicts determining a coolant state based on a history of coolant levels and coolant states.

FIG. 19 provides a routine 1900 for restricting engine operating parameters based on the coolant state determined by routine 1800. Routine 1900 may be executed for each measurement period, for example at 1834 of routine 1800. An engine controller may include a set of restriction modes, and may select a mode from the set of modes based on the coolant state and the duration for which the coolant system has been in that coolant state. Selecting a restriction mode may include one or more of restricting an engine load to be below an upper threshold, reducing an injection pulse-width for one or more fuel injectors by a threshold amount, entirely eliminating fuel injection for one or more fuel injectors, forcing the engine to operate in an idle mode, and displaying messages to the vehicle operator indicating information about the bulk coolant level and about the selected restriction mode. Displaying messages to the vehicle operator may include indicating any limits placed on engine/transmission operation (e.g., limits on power, torque, engine speed, available gears, etc.), as well as indicating that addition of coolant is needed if in a LOW level state, or indicating an immediate need to stop and add coolant if in an EMPTY level state. Selecting a restriction mode may also include tracking the duration for which the engine has operated under the current restriction mode.

Routine 1900 begins at 1902, where the coolant state is retrieved from the engine controller. Retrieving a coolant state may include retrieving a duration for which the current coolant state has been active. At 1904, it is determined whether the coolant state was changed during the current measurement period. If the coolant state was changed, routine 1900 proceeds to 1908, where a restriction mode may be selected based on the coolant state and the duration in the coolant state. Selecting a restriction mode is described below in further detail. If the coolant state was not changed during the current measurement period, routine 1900 proceeds to 1906.

At 1906, the duration for which the current coolant state has been active is compared to one or more threshold durations. Additionally, the duration for which the current restriction mode has been active may be compared to one or more threshold durations. If a threshold duration has not been reached, routine 1900 proceeds to 1910, where operation in the current restriction mode may be maintained. Routine 1900 may then terminate.

Returning to 1906, if a threshold duration has been reached, routine 1900 proceeds to 1908, where a restriction mode may be selected based on the coolant state and the duration in the coolant state. Note that 1908 may also be reached if the coolant state was changed during the current measurement period. In one example, the set of restriction modes the engine controller may select from may include at least a first, second, and third mode. In the first restriction mode, the engine controller may only indicate to the vehicle operator that the bulk coolant level is low and that the vehicle should be taken to a dealership, without placing restrictions on engine operating parameters such as engine load and fuel injection. Selecting the second restriction mode may include placing an upper threshold on engine loads and cutting fuel injection from one or more cylinders by eliminating a fuel injection pulse-width for those cylinders. The third restriction mode may include the restrictions of the second mode, and may further restrict the engine to only operating in an idle mode.

In some examples, operation with a particular restriction mode may not be exited until certain conditions are met. In one example, the second restriction mode may only be exited upon the restarting the engine. Such an example may also include only exiting operation with the third restriction mode upon visiting a dealership. In such examples, selecting a restriction mode at 1908 may also be based on the current restriction mode. For example, the engine may be operating in the second restriction mode and current coolant state may indicate operating in the first restriction mode. However, the engine controller may not select to operate in the first restriction mode based on currently operating in the second restriction mode.

Selecting a restriction mode at 1908 may include, if the coolant state is LOW or EMPTY, selecting the first restriction mode mentioned above. Selecting the first restriction mode may include operating in the first restriction mode for a threshold duration, and selecting one of the second and third restriction modes based on engine conditions after the threshold duration.

Selecting a restriction mode at 1908 may alternately include, if the coolant state has been EMPTY for more than a threshold duration, operating in the second restriction mode. Selecting the second restriction mode may include operating in the second restriction mode for a threshold duration, and selecting the third restriction mode after the threshold duration. The engine controller may also select to operate in the second restriction mode if the last known state of the system was EMPTY and the current state has been UNKNOWN/DEGRADED for a threshold duration, as this condition may be considered functionally equivalent to EMPTY.

Selecting a restriction mode at 1908 may further include, if the coolant state has been EMPTY for more than a threshold duration, operating in the third restriction mode. Selecting the third restriction mode may include operating in the third restriction mode until the vehicle has been taken to a dealership. The engine controller may only select to operate in the third restriction mode when the coolant state is confirmed EMPTY. In this way, engine operating parameters may be restricted to avoid overheating in the engine.

The technical effect of using a system configured with a coolant overflow container having an internal recess to hold fluid and a vertical, hollow tube positioned external to the container and including an internal recess to hold fluid, wherein a bottom-most level of the recess is positioned vertically below a bottom-most level of the internal recess of the container and having a sensor coupled to the bottom-most level of the internal recess of the tube, is that the coolant level in the container can be inferred more accurately. By fluidically coupling the standpipe to the overflow container, fluid levels are allowed to equilibrate in the two containers enabling the fluid height in the container to be reflected in the fluid height of the vertical tube. By estimating the fluid height in the vertical tube using the transmission of ultrasonic signals and detection of their echoes, the sensor output is not grossly affected by distortions that may affect bulk fluid reservoirs, such as temperature and motion variations. In addition, the technical effect of adjusting an estimate of fluid level in the vertical, hollow standpipe based on vehicle motion parameters is that the fluid level can be better compensated for variations due to slosh, and a vehicle actuator can be adjusted in response to the more accurate fluid level estimate. This also reduces erratic fluid level estimates generated due to fluid slosh. By limiting engine power based on the estimated fluid level over a duration, engine overheating due to low coolant levels in the reservoir can be reduced. In addition, unwanted triggering of failure modes due to false low readings can also be averted. By enabling a processor to estimate the fluid level in the standpipe based on raw data and/or processed data generated by the ultrasonic sensor, estimation accuracy and reliability is improved. More specifically, the technical effect of receiving each of unprocessed, raw echo times and processed fluid level data from the sensor coupled in the vertical tube, and generating a fluid level estimate based on the raw echo times and vehicle sensor data during some conditions while generating the fluid level estimate based on the processed data during other conditions raw data that is unreliable can be discarded and not used to estimate the fluid level. This increases the weightage of reliable data in the final estimation. In addition, sensor power output can be optimized based on the nature of raw data collected at the sensor. Specifically, the technical effect of periodically transmitting a sensor signal from a bottom to a top of the vertical tube, receiving an echo of the transmitted signal at the sensor and adjusting a power of the periodically transmitted signals based on an average duration elapsed between the transmitting and the receiving, is that sensor power can be adjusted to improve the number and quality of first order echoes generated while decreasing the number of second order echoes generated. This improves the accuracy and reliability of the fluid level estimate while also providing power reduction benefits. Overall, coolant levels in an engine cooling system can be better monitored, improve engine performance.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method, comprising:
periodically transmitting a sensor signal from a bottom to a top of a vertical, hollow tube fluidically coupled in parallel to a pressurized reservoir of an engine coolant system at each of the bottom and the top;
receiving an echo of the transmitted signal; and
adjusting a power of the periodically transmitted signals based on an average energy of the received echoes.

2. The method of claim 1, wherein the adjusting includes increasing the power of the periodically transmitted signal in response to the average energy being lower than a threshold.

3. The method of claim 1, wherein the adjusting includes increasing the power of the periodically transmitted signal in response to a first order processing of the average energy being lower than a first threshold and a second order processing of the average energy being lower than a second threshold.

4. The method of claim 3, wherein the first and second threshold are based on first and second fixed minimum values.

5. The method of claim 1, further comprising, estimating a state of fluid level in the coolant reservoir based on the average duration between the transmitting and receiving of the sensor signal.

6. The method of claim 5, further comprising, limiting an engine power based on the estimated state.

7. The method of claim 5, further comprising, indicating degradation of the sensor based on the average duration.

8. The method of claim 7, further comprising, in response to the indication of sensor degradation, adjusting the estimated state of fluid level in the coolant reservoir.

9. The method of claim 5, wherein the estimated state of fluid level in the coolant reservoir is further adjusted with a slosh compensation term, the slosh compensation term calculated based on vehicle lateral and longitudinal acceleration.

10. A method, comprising:
adjusting sensor power in response to detection of a second order harmonic echo time, the sensor coupled in a vertical tube aligned parallel to a pressurized reservoir of an engine coolant system, the tube fluidically coupled to the reservoir at each of a top and bottom location.

11. The method of claim 10, wherein the adjusting includes decreasing the sensor power in response to the detected second harmonic time being larger than a threshold.

12. The method of claim 11, further comprising, further adjusting the sensor power in response to the detection of a first order harmonic echo time, the sensor power increased in response to the detected first order harmonic time being smaller than a threshold.

13. The method of claim 12, further comprising, estimating a fluid level in the vertical tube based on each of the first order and the second order echo time; and inferring a fluid level in the reservoir based on the estimated fluid level in the vertical tube.

14. The method of claim 13, wherein the tube is fluidically coupled to the reservoir at each of the top and bottom location via a first and second hose, fluid moving between the vertical tube and the coolant reservoir via the first and second hose, and wherein the vertical tube includes a headspace between the top location and the fluid level in the vertical tube.

15. The method of claim 14, further comprising, estimating a change in the fluid level in the vertical tube based on fluid motion between the vertical tube and the coolant reservoir due to vehicle motion induced slosh, the vehicle motion induced slosh estimated based on the second order harmonic time.

16. A coolant system coupled in a vehicle, comprising:
a coolant overflow container;
a vertical, hollow tube positioned adjacent to the container;
a first hose fluidly coupling a top of the container to a top of the vertical tube; and
a second hose fluidly coupling a bottom of the container to a bottom of the vertical tube, wherein a level of fluid in the container equilibrates with a level of fluid in the vertical tube;
a piezoelectric element coupled to the bottom of the tube;
a processor communicatively coupled to the sensor, the processor configured with computer readable instructions for:
periodically transmitting a signal from the element towards the top of the tube;
estimating a first order harmonic echo time elapsed between the signal being transmitted by the sensor and an echo of the signal being received at the sensor;
processing a second order harmonic time based on the first order harmonic echo time; and
adjusting a power output of the element based on each of the first order and second order harmonic time.

17. The system of claim 16, wherein the processor includes further instructions for: estimating a change in fluid level in the vertical tube due to fluid transfer between the vertical tube and the container via the first and second hose, the fluid transfer due to vehicle lateral and/or longitudinal acceleration, the change estimated based on each of the first order and second order harmonic time.

18. The system of claim 17, wherein the processor includes further instructions for: indicating sensor degradation based on each of the first order and second order harmonic time.

19. The system of claim 18, wherein the processor includes further instructions for limiting an engine power response to the indication of sensor degradation.

* * * * *